(12) United States Patent
Cartledge et al.

(10) Patent No.: US 10,568,732 B2
(45) Date of Patent: *Feb. 25, 2020

(54) SURGICAL IMPLANT DEVICES AND METHODS FOR THEIR MANUFACTURE AND USE

(71) Applicant: Edwards Lifesciences CardiAQ LLC, Irvine, CA (US)

(72) Inventors: Richard George Cartledge, Boca Raton, FL (US); John P. Cartledge, Boca Raton, FL (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,850

(22) Filed: Mar. 23, 2018

(65) Prior Publication Data

US 2018/0206976 A1 Jul. 26, 2018

Related U.S. Application Data

(60) Continuation of application No. 15/213,125, filed on Jul. 18, 2016, now Pat. No. 9,925,033, which is a
(Continued)

(51) Int. Cl.
*A61F 2/06* (2013.01)
*A61B 17/15* (2006.01)
(Continued)

(52) U.S. Cl.
CPC .......... *A61F 2/07* (2013.01); *A61B 17/07207* (2013.01); *A61B 17/115* (2013.01);
(Continued)

(58) Field of Classification Search
CPC ........ A61F 2/07; A61F 2/89; A61F 2002/075; A61F 2/90; A61F 2/954; A61F 2002/077;
(Continued)

(56) References Cited

U.S. PATENT DOCUMENTS 3,409,013 A 11/1968 Berry
3,548,417 A 12/1970 Kisher
(Continued)

FOREIGN PATENT DOCUMENTS

DE 2246526 A1 3/1973
DE 0144167 C 6/1985
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Ann Schillinger
(74) *Attorney, Agent, or Firm* — Klarquist Sparkman, LLC; Joel B. German

(57) ABSTRACT

An implantable vascular device comprises an expandable and compressible implant body, a housing, a rotatable member, and a locking member. The housing is coupled to a first end portion of the implant body. The rotatable member is coupled to the housing and to a second end portion of the implant body such that rotating the rotatable member relative to the housing and the implant body expands or contracts the implant body. The locking member is coupled to the rotatable member and configured to move between an unlocked state and a locked state. In the unlocked state, the locking member allows the rotatable member to be rotated relative to the housing and the implant body. In the locked state, the locking member prevents the rotatable member from being rotated relative to the housing and the implant body.

20 Claims, 17 Drawing Sheets

Related U.S. Application Data division of application No. 12/822,291, filed on Jun. 24, 2010, now Pat. No. 9,408,607.

(60) Provisional application No. 61/222,646, filed on Jul. 2, 2009.

(51) Int. Cl.
| | |
|---|---|
| A61F 2/07 | (2013.01) |
| A61B 17/072 | (2006.01) |
| A61F 2/954 | (2013.01) |
| A61F 2/958 | (2013.01) |
| A61F 2/966 | (2013.01) |
| A61F 2/848 | (2013.01) |
| A61F 2/89 | (2013.01) |
| A61B 17/115 | (2006.01) |
| A61F 2/90 | (2013.01) |
| A61F 2/95 | (2013.01) |

(52) U.S. Cl.
CPC .............. *A61F 2/06* (2013.01); *A61F 2/848* (2013.01); *A61F 2/89* (2013.01); *A61F 2/954* (2013.01); *A61F 2/958* (2013.01); *A61F 2/966* (2013.01); *A61B 17/1155* (2013.01); *A61B 2017/07228* (2013.01); *A61B 2017/1157* (2013.01); *A61F 2/90* (2013.01); *A61F 2002/061* (2013.01); *A61F 2002/077* (2013.01); *A61F 2002/8483* (2013.01); *A61F 2002/8486* (2013.01); *A61F 2002/9534* (2013.01); *A61F 2220/0016* (2013.01); *A61F 2250/001* (2013.01)

(58) Field of Classification Search
CPC ...... A61F 2250/0039; A61F 2220/0016; A61F 2002/9511; A61F 2/06; A61F 2/848; A61F 2/966; A61F 2002/8483; A61F 2250/0069; A61F 2/82; A61F 2002/9517; A61F 2002/9534; A61F 2/2418; A61F 2/2439; A61F 2/243
See application file for complete search history.

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |

(56) References Cited

U.S. PATENT DOCUMENTS

| | | |
|---|---|---|
| 6,302,906 B1 | 10/2001 | Goicoechea et al. |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,875,231 B2 | 4/2005 | Anduiza et al. |
| 6,878,162 B2 | 4/2005 | Bales et al. |
| 6,893,459 B1 | 5/2005 | Macoviak |
| 6,893,460 B2 | 5/2005 | Spenser et al. |
| 6,908,481 B2 | 6/2005 | Cribier |
| 6,936,067 B2 | 8/2005 | Buchanan |
| 6,951,571 B1 | 10/2005 | Srivastava |
| 7,018,406 B2 | 3/2006 | Seguin et al. |
| 7,018,408 B2 | 3/2006 | Bailey et al. |
| 7,041,132 B2 | 5/2006 | Quijano et al. |
| 7,096,554 B2 | 8/2006 | Austin et al. |
| 7,225,518 B2 | 6/2007 | Eidenschink et al. |
| 7,235,093 B2 | 6/2007 | Gregorich |
| 7,258,696 B2 | 8/2007 | Rabkin et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,326,236 B2 | 2/2008 | Andreas et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,887,583 B2 | 2/2011 | Macoviak |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,226,707 B2 | 7/2012 | White |
| 8,291,570 B2 | 10/2012 | Eidenschink et al. |
| 8,449,606 B2 | 5/2013 | Eliasen et al. |
| 8,454,685 B2 | 6/2013 | Hariton et al. |
| 8,647,378 B2 | 2/2014 | Mews et al. |
| 8,652,203 B2 | 2/2014 | Quadri et al. |
| 8,685,080 B2 | 4/2014 | White |
| 8,747,463 B2 | 6/2014 | Fogarty et al. |
| 8,852,261 B2 | 10/2014 | White |
| 9,039,756 B2 | 5/2015 | White |
| 9,078,781 B2 | 7/2015 | Ryan et al. |
| 9,259,314 B2 | 2/2016 | White |
| 9,408,607 B2 * | 8/2016 | Cartledge ........ A61B 17/07207 |
| 9,566,178 B2 | 2/2017 | Cartledge et al. |
| 9,913,716 B2 | 3/2018 | Cartledge et al. |
| 2001/0002445 A1 | 5/2001 | Vesely |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0173842 A1 | 11/2002 | Buchanan |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0096736 A1 | 5/2005 | Osse et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288771 A1 | 12/2005 | Majercak et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2006/0212113 A1 | 9/2006 | Shaolian et al. |
| 2006/0229719 A1 | 10/2006 | Marquez et al. |
| 2006/0259137 A1 | 11/2006 | Artof et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0032850 A1 | 2/2007 | Ruiz et al. |
| 2007/0073389 A1 | 3/2007 | Bolduc et al. |
| 2007/0112422 A1 | 5/2007 | Dehdashtian |
| 2007/0142907 A1 | 6/2007 | Moaddeb et al. |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2007/0276478 A1 | 11/2007 | Marmureanu et al. |
| 2008/0027483 A1 | 1/2008 | Cartledge et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0275537 A1 | 11/2008 | Limon |
| 2009/0062825 A1 | 3/2009 | Pool et al. |
| 2009/0099638 A1 | 4/2009 | Grewe |
| 2009/0099650 A1 | 4/2009 | Bolduc et al. |
| 2009/0125118 A1 | 5/2009 | Gong |
| 2009/0157162 A1 | 6/2009 | Chow et al. |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0168844 A1 | 7/2010 | Toomes et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0066224 A1 | 3/2011 | White |
| 2011/0093060 A1 | 4/2011 | Cartledge et al. |
| 2011/0098804 A1 | 4/2011 | Yeung et al. |
| 2011/0219603 A1 | 9/2011 | White |
| 2011/0224781 A1 | 9/2011 | White |
| 2011/0230956 A1 | 9/2011 | White |
| 2011/0245918 A1 | 10/2011 | White |
| 2011/0288629 A1 | 11/2011 | White |
| 2011/0319991 A1 | 12/2011 | Hariton et al. |
| 2012/0089217 A1 | 4/2012 | Mews et al. |
| 2012/0123529 A1 | 5/2012 | Levi et al. |
| 2012/0259409 A1 | 10/2012 | Nguyen et al. |
| 2012/0323316 A1 | 12/2012 | Chau et al. |

(56) References Cited

U.S. PATENT DOCUMENTS

| | | |
|---|---|---|
| 2013/0023985 A1 | 1/2013 | Khairkhahan et al. |
| 2013/0046373 A1 | 2/2013 | Cartledge et al. |
| 2013/0158656 A1 | 6/2013 | Sutton et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310923 A1 | 11/2013 | Kheradvar et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0018911 A1 | 1/2014 | Zhou et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0201918 A1 | 7/2015 | Kumar et al. |
| 2015/0257779 A1 | 9/2015 | Sinelnikov et al. |
| 2017/0160152 A1 | 6/2017 | Hamel et al. |

FOREIGN PATENT DOCUMENTS

| | | |
|---|---|---|
| DE | 19532846 A1 | 3/1997 |
| DE | 19546692 A1 | 6/1997 |
| DE | 19728337 A1 | 1/1999 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1557138 A1 | 7/2005 |
| EP | 1570809 A1 | 9/2005 |
| EP | 1796597 A2 | 6/2007 |
| EP | 2033593 A1 | 3/2009 |
| EP | 2438872 A1 | 4/2012 |
| EP | 3311783 A1 | 4/2018 |
| EP | 2768429 B1 | 5/2018 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9626689 A1 | 9/1996 |
| WO | 9724080 A1 | 7/1997 |
| WO | 9727959 A1 | 8/1997 |
| WO | 9829057 A1 | 7/1998 |
| WO | 9853760 A2 | 12/1998 |
| WO | 9930646 A1 | 6/1999 |
| WO | 9933414 A1 | 7/1999 |
| WO | 99/40964 A1 | 8/1999 |
| WO | 99/47075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0154624 A1 | 5/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 02076348 A1 | 10/2002 |
| WO | 03018100 A1 | 3/2003 |
| WO | 03047468 A1 | 6/2003 |
| WO | 2004045450 A2 | 6/2004 |
| WO | 2005034812 | 4/2005 |
| WO | 2005055883 A1 | 6/2005 |
| WO | 2005062980 A2 | 7/2005 |
| WO | 2005084595 A1 | 9/2005 |
| WO | 2006014233 A2 | 2/2006 |
| WO | 2006014347 A1 | 2/2006 |
| WO | 2006032051 A2 | 3/2006 |
| WO | 2006034008 A2 | 3/2006 |
| WO | 2006105084 A2 | 10/2006 |
| WO | 2006111391 A1 | 10/2006 |
| WO | 2006127089 A1 | 11/2006 |
| WO | 2006138173 A3 | 3/2007 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008016578 A2 | 2/2008 |
| WO | 2008035337 A2 | 3/2008 |
| WO | 2008091515 A2 | 7/2008 |
| WO | 2008097999 A2 | 8/2008 |
| WO | 2008140796 A1 | 11/2008 |
| WO | 2008147964 A1 | 12/2008 |
| WO | 2008150529 A1 | 12/2008 |
| WO | 2009033469 A1 | 3/2009 |
| WO | 2010011699 A2 | 1/2010 |
| WO | 2010121076 A2 | 10/2010 |
| WO | 2013059776 A1 | 4/2013 |
| WO | 2013126529 A2 | 8/2013 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

* cited by examiner

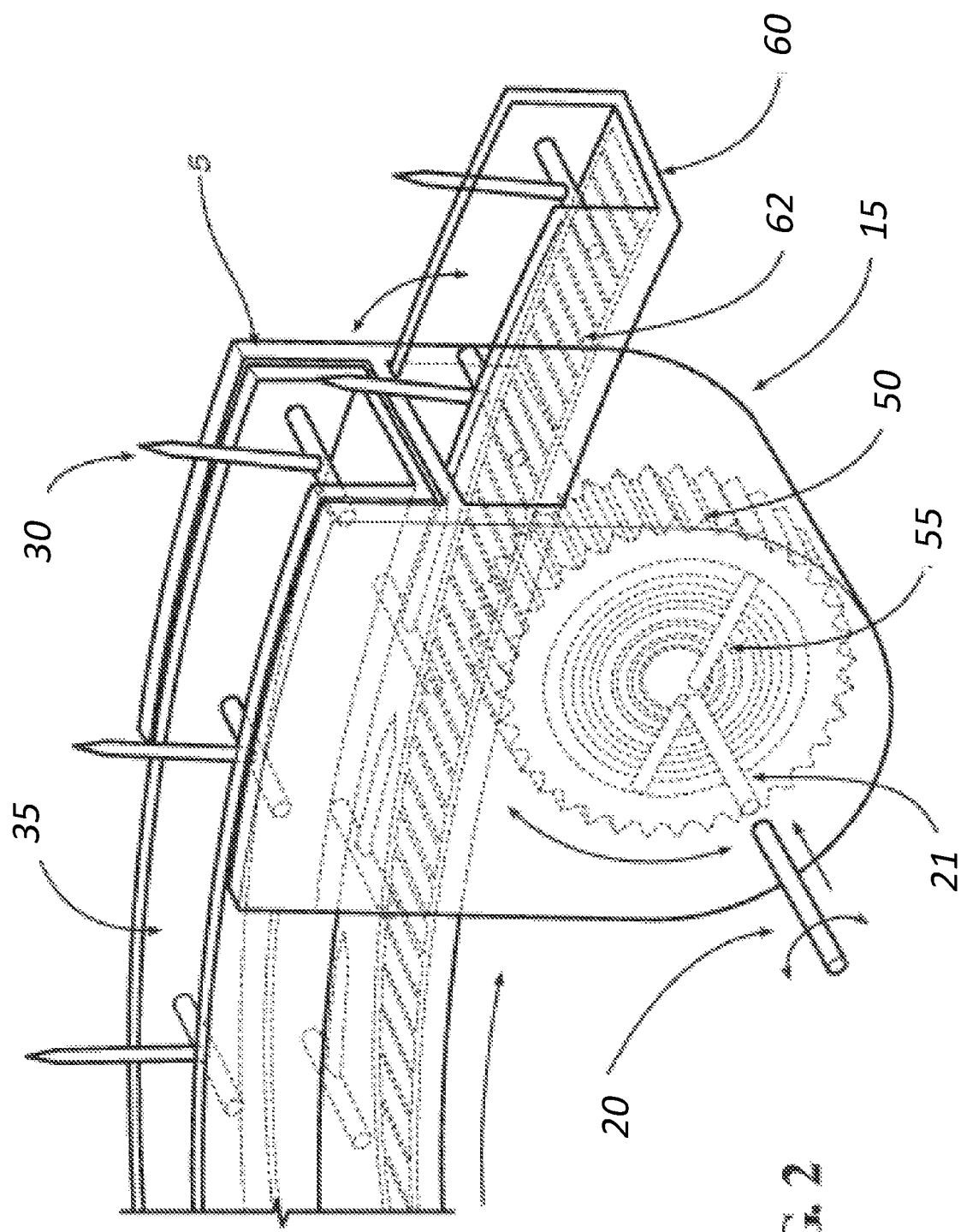

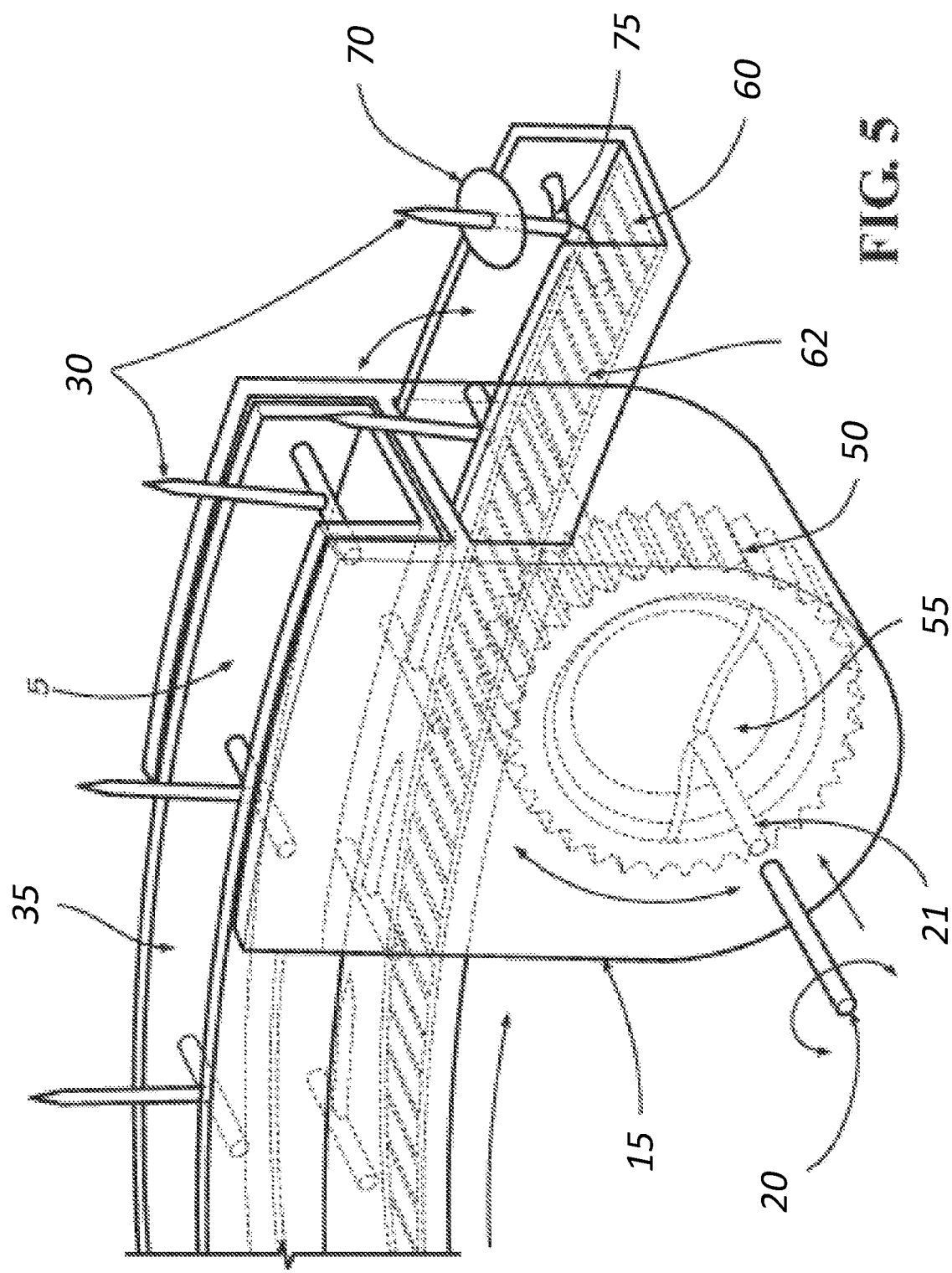

SURGICAL IMPLANT DEVICES AND METHODS FOR THEIR MANUFACTURE AND USE

CROSS REFERENCE TO RELATED APPLICATION

This application is a continuation of U.S. patent application Ser. No. 15/213,125, filed Jul. 18, 2016, now U.S. Pat. No. 9,925,033, which is a divisional of U.S. patent application Ser. No. 12/822,291, filed on Jun. 24, 2010, now U.S. Pat. No. 9,408,607, which claims the benefit of U.S. Provisional Application No. 61/222,646, filed on Jul. 2, 2009, the entire disclosures of which are hereby incorporated herein by reference in their entirety.

FIELD OF THE INVENTION

The present disclosure relates to the field of surgical implant devices and method for their manufacture and use. In particular, this disclosure relates to medical devices applicable to vascular surgery and the treatment of aneurysms or other luminal defects in other anatomic conduits.

BACKGROUND OF THE INVENTION

Medical and surgical implants are often placed in anatomic spaces where it is desirable for the implant to conform to the unique anatomy of the targeted anatomic space to secure a seal therein, preferably without disturbing or distorting the unique anatomy of said targeted anatomic space.

While the lumens of most hollow anatomic spaces are ideally circular, in fact the cross-sectional configurations of most anatomic spaces are at best ovoid, and may be highly irregular. Lumenal irregularity may be due to anatomic variations and/or to pathologic conditions that may change the shape and topography of the lumen and its associated anatomic wall.

Examples of anatomic spaces where such implants may be deployed include, but are not limited to, blood vessels, the heart, other vascular structures, vascular defects, the trachea, the oropharynx, the esophagus, the stomach, the duodenum, the ileum, the jejunum, the colon, the rectum, ureters, urethras, fallopian tubes, biliary ducts, pancreatic ducts, or other anatomic structures containing a lumen used for the transport of gases, blood, or other liquids or liquid suspensions within a mammalian body.

Among vascular effects that are addressed by some preferred embodiments of the present disclosure are thoracic and abdominal aortic aneurysms.

In order for a patient to be a candidate for existing endograft methods and technologies, a proximal neck of at least 15 mm of normal aorta must exist between the origin of the most inferior renal artery and the origin of the aneurysm in the case of abdominal aneurysms or the left subclavian artery for thoracic aortic aneurysms in order to permit an adequate seal. Similarly, at least 15 mm of normal vessel must exist distal to the distal extent of the aneurysm for an adequate seal to be achieved.

Migration of existing endografts has also been a significant clinical problem, potentially causing leakage and re-vascularization of aneurysms and/or compromising necessary vascular supplies to arteries such as the carotid, subclavian, renal, or internal iliac vessels. This problem has been partially addressed by some existing endograft designs, in which barbs or hooks have been incorporated to help retain the endograft at its intended site. However, these existing endograft designs are not removable and repositionable once they are deployed. Thus, once such an endograft has been placed, open surgery is necessary if there is failure due to leakage or undesired occlusion of other vascular structures.

Because of the limitations imposed by existing vascular endograft devices and endovascular techniques, approximately eighty percent of abdominal and thoracic aneurysms repaired in the U.S. are still managed though open vascular surgery, instead of the lower morbidity of the endovascular approach.

SUMMARY OF THE INVENTION

Implant devices according to the present disclosure are provided with one or more improvements that increase the ability of such an implant to be precisely deployed or re-deployed, with better in situ accommodation to the local anatomy of the targeted anatomic site, and/or with the ability for post-deployment adjustment to accommodate anatomic changes that might compromise the efficacy of the implant.

One aspect of the present disclosure is directed towards novel designs for endovascular implant grafts, and methods for their use for the treatment of aortic aneurysms and other structural vascular defects. A sealable, repositionable endograft system for placement in a blood vessel is disclosed, in which an endograft implant comprises a non-elastic tubular implant body with an elastic proximal ends and an elastic distal end(s). Both the elastic proximal and distal ends in an implant according to the present disclosure further comprise one or more circumferential sealable collars and one or more variable sealing device, capable of controllably varying the expanded diameter of said collar upon deployment to achieve the desired seal between the collar and the vessel's inner wall. An endovascular implant according to the present disclosure further comprises a central lumen and one or more control leads extending distally from releasable connections with each variable sealing device. Embodiments of endovascular implants according to the present disclosure may further be provided with retractable retention tines or other retention devices allowing an implant to be repositioned before final deployment. An endograft system according to the present disclosure further comprises a delivery catheter with an operable tubular sheath, capable of housing a folded or compressed endograft implant prior to deployment and capable of retracting or otherwise opening in at least its proximal end to allow implant deployment, said sheath sized and configured to allow its placement via a peripheral arteriotomy site, and of appropriate length to allow its advancement into the thoracic or abdominal aorta, as required for a specific application.

Post-implantation remodeling of the aortic neck proximal to an endovascular graft (endograft) has been reported. While this phenomenon may be due to aortic wall injury caused by the over-dilatation (typically 110%) of the aorta to deploy the metallic lattice that supports such endografts, existing endograft technology does not allow for the management of this condition without placement of an additional endograft sleeve to cover the remodeled segment, again requiring the over-dilatation for deployment.

Endografts of the present disclosure do not require balloon over-dilatation for their deployment. Moreover, the improvements in implant design described herein allow for better accommodation by the implant of the local anatomy, as opposed to altering the local anatomy to conform to the implant as is the presently accepted practice. Finally, implants with improvements of the present disclosure may be provided with means to change the implant configuration post-initial deployment, allowing for manual adaptation to any future anatomic remodeling at the implantation site.

The preceding description is presented only as an exemplary application of the devices and methods according to the present disclosure.

BRIEF DESCRIPTION OF THE DRAWINGS

FIG. 2 is a detailed view of an embodiment of an implant interface with a coil spring drive gear design according to the present disclosure.

FIG. 5 is a detailed view of an embodiment of an implant interface with an electromagnetic re-docking mechanism and spring-loaded remodeling attachment members according to the present disclosure.

DETAILED DESCRIPTION OF DISCLOSED EMBODIMENTS

Figure 1A:
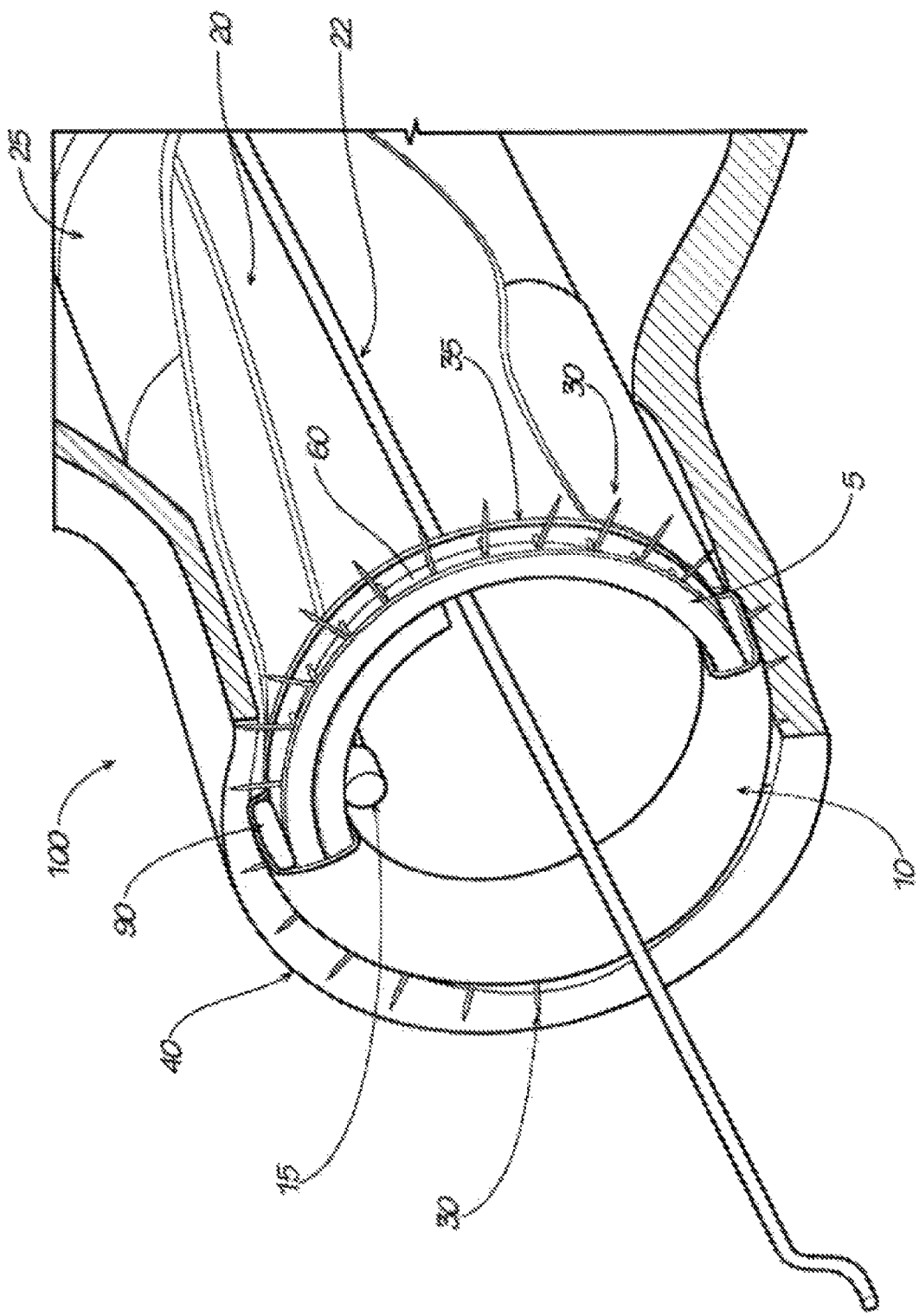
FIG. 1A is a perspective view of an embodiment of an implant interface according to the present disclosure.

The present disclosure may be understood more readily by reference to the following detailed description of the preferred embodiments described herein and the examples included herein. However, before the preferred embodiments of the devices and methods according to the present disclosure are described, it is to be understood that this disclosure is not limited to the exemplary embodiments described within this disclosure, and the numerous modifications and variations therein that will be apparent to those skilled in the art remain within the scope of the disclosure provided herein. It is also to be understood that the terminology used herein is for the purpose of describing specific embodiments only and is not intended to be limiting.

Unless otherwise noted, the terms used herein are to be understood according to conventional usage by those of ordinary skill in the relevant art. In addition to the definitions of terms provided below, it is to be understood that as used in the specification and in the claims, "a" or "an" can mean one or more, depending upon the context in which it is used.

Certain aspects of the present disclosure are directed towards novel designs for sealable and repositionable endovascular implant grafts, and methods for their use for the treatment of aortic aneurysms and other structural vascular defects.

In an exemplary embodiment according to the present disclosure, a sealable vascular endograft system for placement in a vascular defect is provided, comprising an elongated main implant delivery catheter with an external end and an internal end for placement in a blood vessel with internal walls. In such an exemplary embodiment, the main implant delivery catheter further comprises a main implant delivery catheter sheath which may be openable or removable at said internal end and a main implant delivery catheter lumen containing within a compressed or folded endovascular implant. Further in such an exemplary embodiment, an endovascular implant comprises a non-elastic tubular implant body with an elastic proximal end terminating in a proximal sealable circumferential collar controlled by a proximal variable sealing device which is operated by a proximal control lead that traverses said main implant delivery catheter and exits at said external end for interface by an operator, such that said proximal sealable circumferential collar may be expanded or contracted by said operator to achieve a fluid-tight seal between said proximal sealable circumferential collar and the internal walls of said blood vessel proximal to said vascular defect. Moreover, in such an exemplary embodiment, an endovascular implant further comprises a non-elastic tubular implant body with an elastic distal end terminating in a distal sealable circumferential collar controlled by a distal variable sealing device which is operated by a distal control lead that exits said main implant delivery catheter at said external end for interface by an operator, such that said distal sealable circumferential collar may be expanded or contracted by said operator to achieve a fluid-tight seal between said distal sealable circumferential collar and the internal walls of said blood vessel distal to the vascular defect.

In an alternate exemplary embodiment of the present disclosure, an endovascular implant comprises a non-elastic tubular implant body with an elastic proximal end terminating in a proximal sealable circumferential collar controlled by a proximal variable sealing device which is operated by a proximal control lead that traverses said main implant delivery catheter and exits at said external end for interface by an operator, such that said proximal sealable circumferential collar may be expanded or contracted by said operator to achieve a fluid-tight seal between said proximal sealable circumferential collar and the internal walls of said blood vessel proximal to said vascular defect. Moreover, in such an exemplary embodiment, an endovascular implant further comprises a non-elastic tubular implant body with an elastic distal end with a distal elastic circumferential collar of an expandable mesh or lattice formation that may be expanded by intralumenal balloon dilatation by said operator to achieve a fluid-tight seal between said distal elastic circumferential collar and the internal walls of said blood vessel distal to the vascular defect. In such an embodiment, particularly in the iliac arteries, the distal aspect of the endograft requires less pressure for an effective seal, and more length of arterial wall is usually available to allow an expandable mesh collar to be employed, compared with the proximal seal which often may be required to accommodate a shortened and/or angulated aortic neck.

In yet another embodiment of the present disclosure, the distal seal, particularly in the iliac arteries, may be effected using a self-expanding mesh endoskeleton or exoskeleton collar attached to the elastic distal end, provided such that the self-expanding mesh endoskeleton or exoskeleton collar is designed such that longitudinal traction on the deployed mesh causes the mesh to elongate and reduce its circumference. This would allow instrumentation to be inserted such as a hook that could adjust the distal seal location post implant deployment. Again, in such an embodiment, particularly in the iliac arteries, the distal aspect of the endograft requires less pressure for an effective seal, and more length of arterial wall is usually available to allow a self-expanding mesh endoskeleton or exoskeleton collar to be employed, compared with the proximal seal which often must accommodate a shortened and/or angulated aortic neck.

Exemplary endografts of the present disclosure comprising self-expanding mesh endoskeleton or exoskeleton collar may further comprise retention tines of any shape with or without barbs for better retention against the receiving vessel walls. Moreover, the retention tines in such endografts of the present disclosure may be provided as separate components that are affixed to the self-expanding mesh endoskeleton or exoskeleton collars, or they may be fabricated as integral components thereof.

In a further exemplary embodiment according to the present disclosure, an implant interface is provided for a sealable attachment of an implant to a wall within the lumen of a blood vessel or other anatomic conduit.

In a yet further exemplary embodiment according to the present disclosure, an implant interface is provided for a sealable attachment of an implant to a wall within the lumen of a blood vessel or other anatomic conduit, wherein the sealable attachment provides for auto-adjustment of the seal while maintaining wall attachment to accommodate post-implantation wall remodeling.

In a still further exemplary embodiment according to the present disclosure, an implant interface is provided for a sealable attachment of an implant to a wall within the lumen of a blood vessel or other anatomic conduit, wherein the sealable attachment provides for a re-docking mechanism to allow post-implantation correction of seal defects.

Yet other exemplary embodiments of endografts and endograft delivery systems according to the present disclosure have steering mechanisms that allow an operator to remotely angulate the implant as desired for difficult anatomic site requirements. Still other exemplary embodiments of endografts and endograft delivery systems according to the present disclosure serve as universal endograft cuffs, being first placed to offer their advantageous anatomic accommodation capabilities, and then serving as a recipient vessel for other endografts, including conventional endografts.

Further exemplary embodiments of endografts according to the present disclosure provide for endovascular treatment of complex anatomic vascular pathologies involving the aortic arch including aneurysms and dissecting aneurysms of the aortic arch.

Referring now in more detail to the drawings, in which like numerals indicate like elements throughout the several views, FIG. 1A shows a proximal circumferential sealable implant interface 100 according to the present disclosure, comprising a sealer belt 60, sealer belt channel side walls 5 provided in an overlapping loop and with a sealer belt channel 35 therewithin, a plurality of retention tines 30 and a compressive foam gasket 90 within said sealer belt channel 35, and a sealing device housing 15, all contained within an elastic sealable collar 10 which is shown in the embodiment of FIG. 1A joined to and continuous with a tubular graft main body 25.

FIG. 1A further shows the proximal circumferential sealable implant interface 100 in place within the lumen defined by an aortic wall 40, and with an injection dye catheter 22 traversing the sealable implant interface 100 and adjoining tubular graft main body 25. Imbedded retention tines 30 are shown within the aortic wall 40. Also shown in FIG. 1A is a control lead 20 extending distally from its attachment to the sealing device housing 15 to exit through an arteriotomy site for operative control by an operator (not shown in FIG. 1A).

In alternate embodiments of the present disclosure not shown in FIGS. 1A-11 herein, a circumferential sealable implant may comprise a freestanding implant which is coupled with or otherwise affixed to a tubular graft at the time of implantation.

Figure 1B:
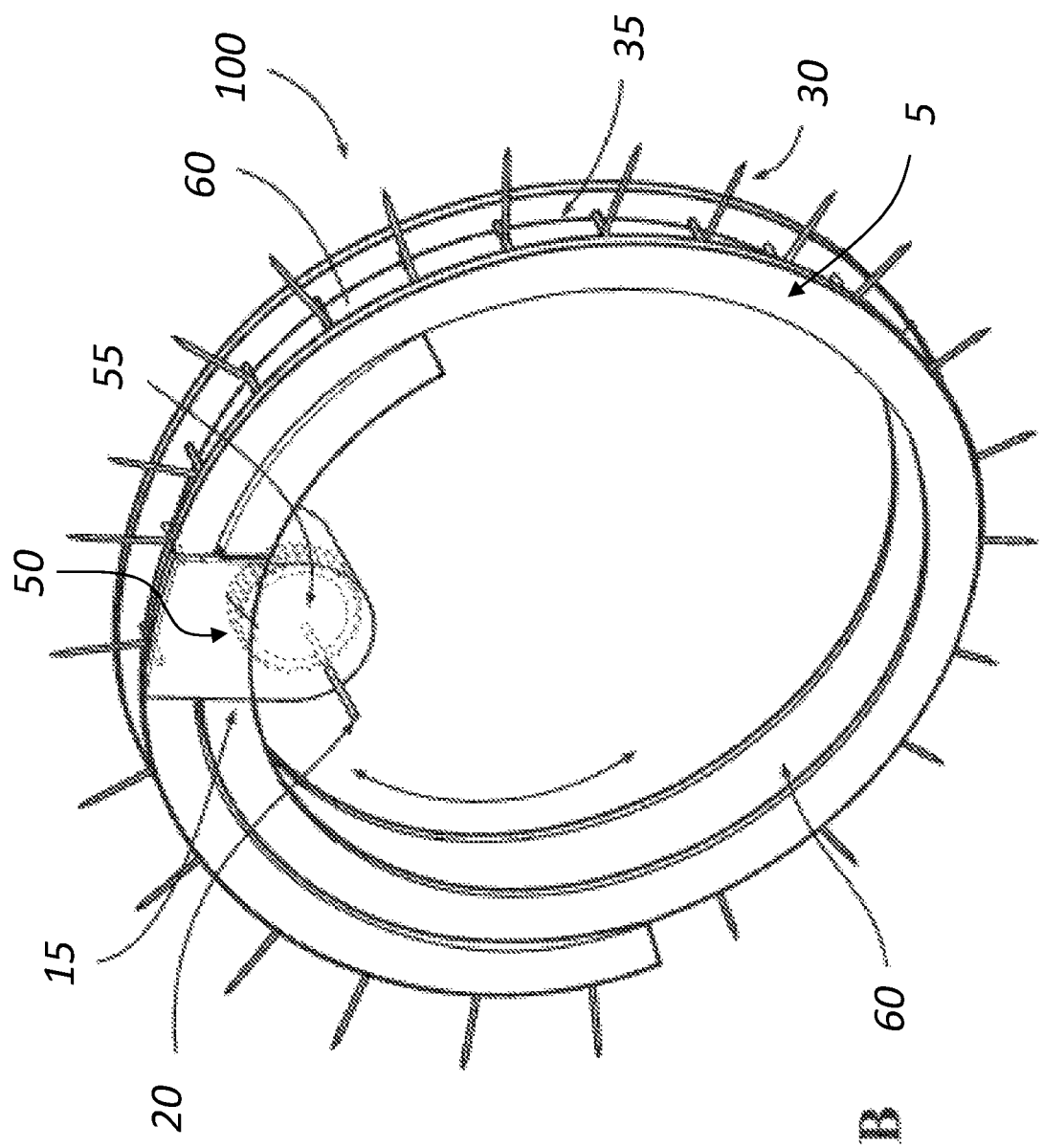
FIG. 1B is a detailed view of an embodiment of an implant interface according to the present disclosure.

FIG. 1B shows a detailed view of one embodiment of a sealable implant interface according to the present disclosure. In FIG. 1B, the sealable implant interface 100 comprises a sealer belt 60 and sealer belt channel side walls 5 provided in an overlapping loop and with a sealer belt channel 35 therewithin to contain a plurality of retention tines 30 and a compressive foam gasket [not shown in FIG. 1B], and a sealing device housing 15. Within said sealing device housing 15, a sealer gear 50 is rotatably mounted to interface with sealer gear retainment slots [not shown in FIG. 1B] located on the sealer belt 60, such that rotation of the sealer gear 50 by operator action on an attached control lead 20 may cause movement of said sealer belt 60 with respect to said sealer gear 50.

In the embodiment shown in FIG. 1B, the sealer gear 50 is further provided with a spring interface 55 with said control lead 20, such that an operator first depresses the spring interface 55 with said control lead 20 to allow rotation of the sealer gear 50 and resultant movement of the sealer belt 60. When the spring interface 55 is not depressed, rotation of the sealer gear 50 is blocked by action of a locking member (not shown in FIG. 1B).

FIG. 2 provides a more detailed view of an embodiment of the coil spring drive gear design of the sealer gear mechanism described in FIG. 1B. FIG. 2 shows a sealer belt 60, sealer belt channel side walls 5 provided in an overlapping loop and with a sealing device housing 15 and a sealer belt channel 35 with a plurality of uniformly distributed sealer gear retainment slots 62 therewithin configured to receive the teeth of a sealer gear 50. The sealer belt channel 35 is provided to contain a plurality of retention tines 30 and a compressive foam gasket [not shown in FIG. 2].

The sealer belt 60 as shown in FIG. 2 and in all other embodiments of the present disclosure may be fabricated of any suitably strong biocompatible material, including, but not limited to titanium, stainless steel, cobalt chromium alloys, other metals, other metal alloys, plastics, or ceramics.

FIG. 2 further illustrates an embodiment in which the retention tines 30 are pivotably mounted within said sealer belt channel 35 to permit their folding within said channel 35 within the overlapping segments of the sealer belt 60.

The coil spring drive gear design of the sealer gear 55 is also detailed in FIG. 2. Pressure transmitted by an operator through a control lead 20 to the central axel 21 of the sealer gear 50 first depresses the spring interface 55 within said sealer gear, allowing the sealer gear to rotate upon subsequent receipt of rotational forces applied by said user to said control lead 20.

Figure 3:
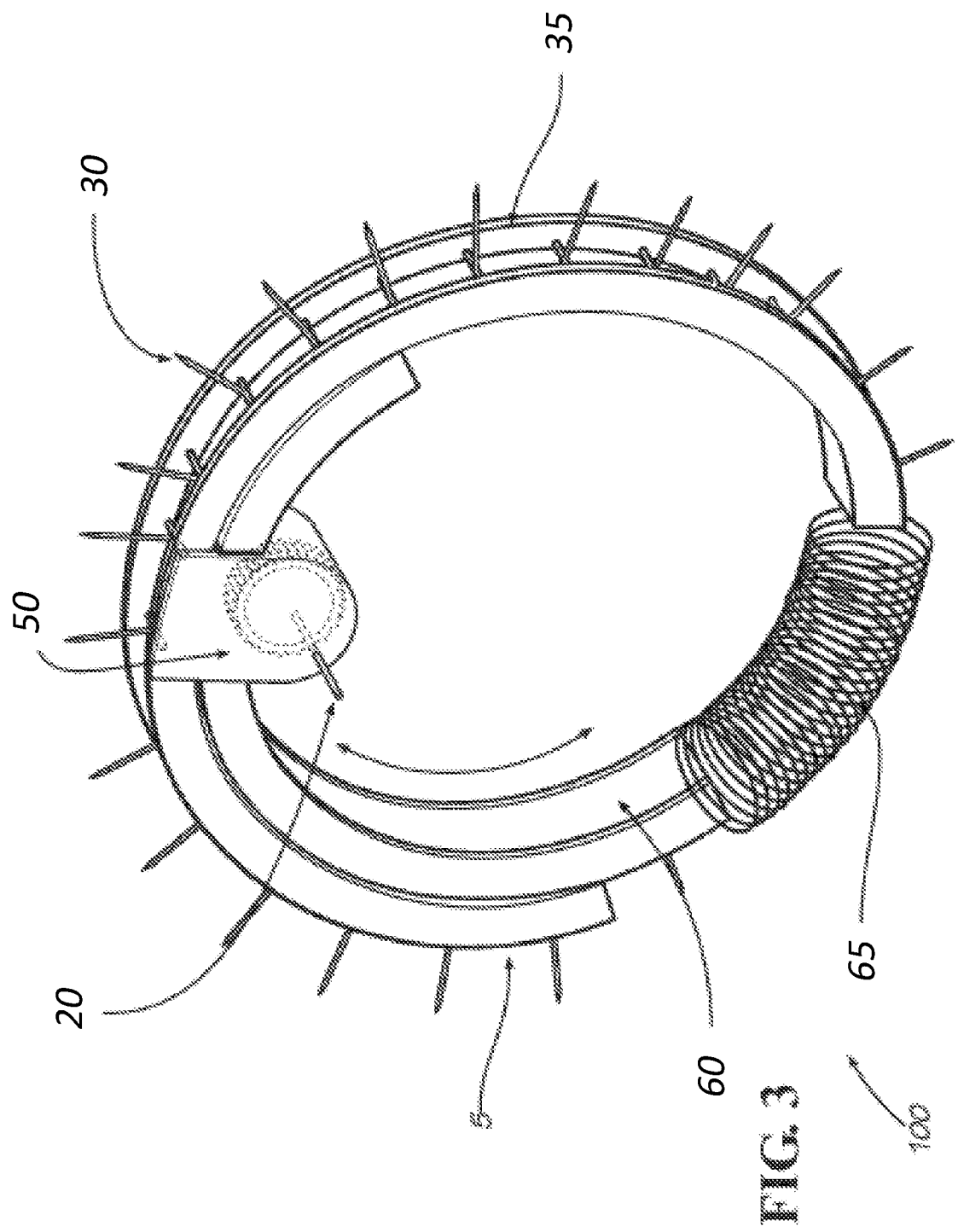
FIG. 3 is a perspective view of an embodiment of an implant interface with an uncompressed spring interposition mechanism according to the present disclosure.

FIG. 3 shows a perspective view of an embodiment of an implant interface with an uncompressed spring interposition mechanism according to the present disclosure. The exemplary sealable implant interface 100 as shown in FIG. 3 resembles the embodiment of FIG. 1B, with a sealer belt 60, sealer belt channel side walls 5 provided in an overlapping loop and with a sealer belt channel 35 therewithin to contain a plurality of retention tines 30 and a compressive foam gasket [not shown in FIG. 1B], and a sealing device housing 15. Within said sealing device housing 15, a sealer gear 50 is rotatably mounted to interface with sealer gear retainment slots [not shown in FIG. 3] located on the sealer belt 60, such that rotation of the sealer gear 50 by operator action on an attached control lead 20 may cause movement of said sealer belt 60 with respect to said sealer gear 50.

In the embodiment of FIG. 3, however, a segment of sealer belt 60 is replaced by an interposed and attached coiled spring 65 shown in a decompressed state. In use, motion imparted to the sealer gear 50 of the sealable implant interface 100 of FIG. 3 may serve to compress or decompress the spring 65.

Figure 4:
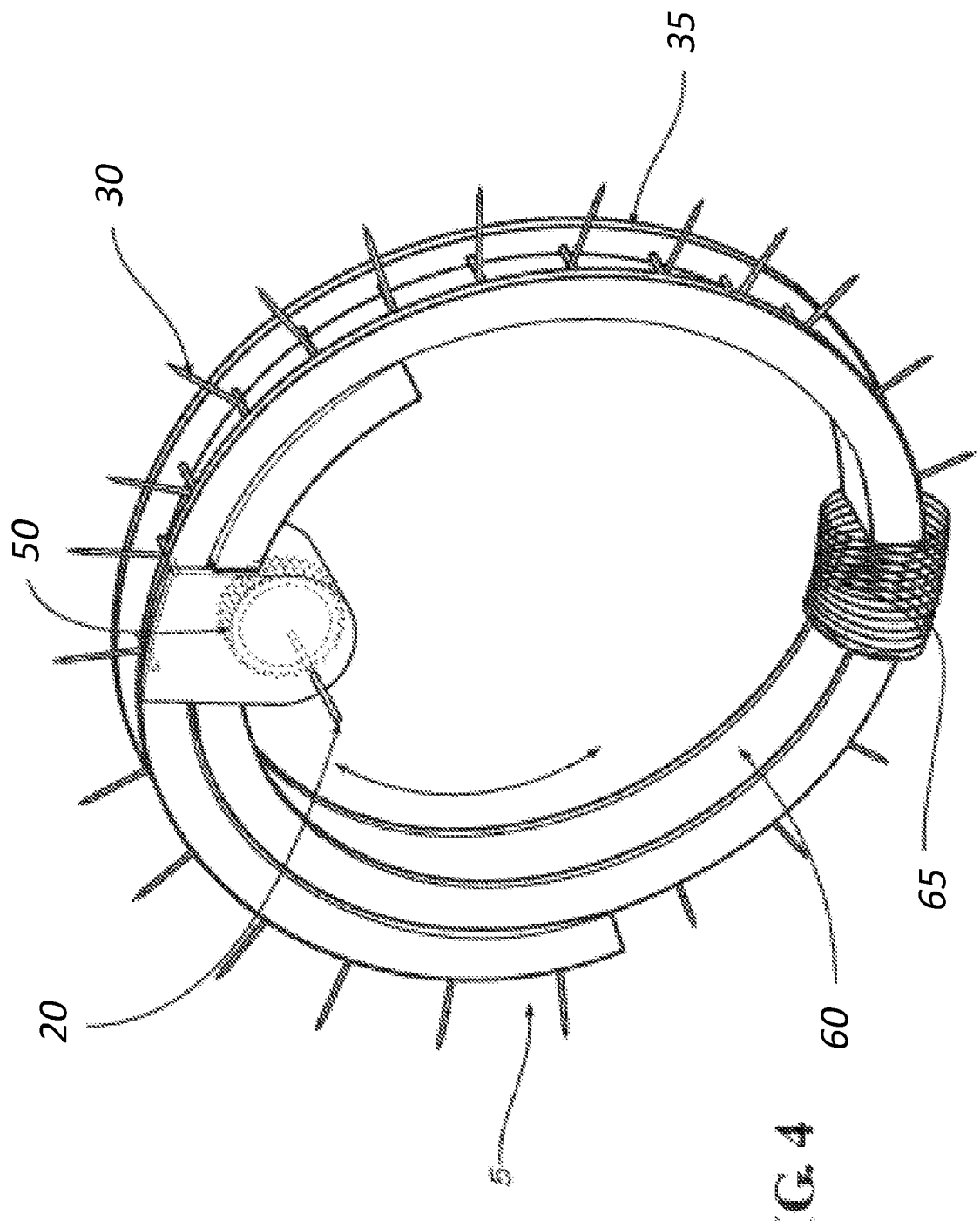
FIG. 4 is a perspective view of an embodiment of an implant interface with a compressed spring-tine mechanism according to the present disclosure.

FIG. 4 shows the same embodiment of an implant interface as FIG. 3, but with a compressed spring-tine mechanism. Compression of the spring 65 creates and maintains radial tension that allows such an embodiment of the present disclosure to automatically provide a fixed amount of adjustment in the event of post-implantation remodeling and dilation of the aorta or recipient blood vessel or anatomic conduit.

FIG. 5 provides a detailed view of an alternate embodiment of an implant interface with an electromagnetic re-docking mechanism and spring-loaded remodeling attachment members according to the present disclosure. In FIG. 5 a detail of an implant interface comprises sealer belt 60 with side walls 5 provided in an overlapping loop and with a sealer belt channel 35 therewithin to contain a plurality of retention tines 30, a plurality of uniformly distributed sealer gear retainment slots 62 therewithin configured to receive the teeth of a sealer gear 50, and a compressive foam gasket [not shown in FIG. 5], and a sealing device housing 15 containing a sealer gear 50.

Also in FIG. 5, a coil spring drive gear design of the sealer gear 55 is also detailed. Pressure transmitted by an operator through a control lead 20 attached to the central axel 21 of the sealer gear 50 first depresses a spring interface 55 within said sealer gear, allowing the sealer gear to rotate upon subsequent receipt of rotational forces applied by said user to said control lead 20.

Furthermore, FIG. 5 shows one of more retention tines 30 pivotably attached to the side walls 63 of the sealer belt 60, such that advancement or retraction of the sealer belt 60 by rotational action of the sealer gear causes said tines to either extend outwardly from said sealer belt 60 or retract within the sealer belt channel 35 when the circumference of the sealer belt 60 is made smaller. In the embodiment shown in FIG. 5, one or more of the retention tines 30 may be further provided with a tine limiter element 70 which serves to limit the depth to which the retention tine 30 may be extended into the wall of the recipient blood vessel or other anatomic conduit.

In addition, as shown in FIG. 5, one or more of the retention tines 30 may be attached to the sealer belt 60 with a pre-tensioned tine mounting element 75 (also called pre-tensioned spring element 75, throughout) that serves to exert an outward radial force on its related retention tine 30 upon deployment.

FIGS. 6A-6D provides detailed views of several exemplary embodiments of spring-loaded remodeling attachment members according to the present disclosure.

Figure 6A:
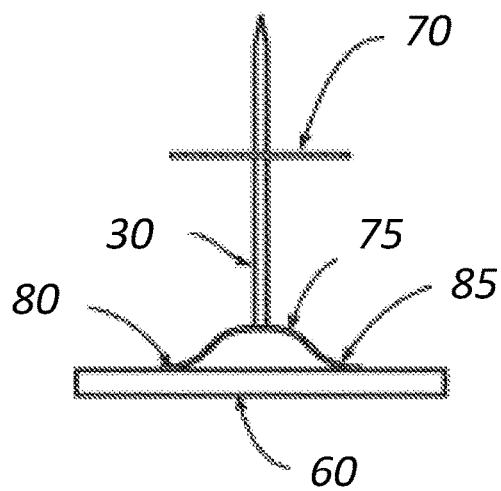
FIGS. 6A-6D are detailed views of several exemplary embodiments of spring-loaded remodeling attachment members according to the present disclosure.

FIG. 6A shows a sealer belt 60 with a retention tine 30 mounted at an erect angle thereto, said retention tine 30 further comprising a tine limiter element 70 which serves to limit the depth to which the retention tine 30 may be extended into the wall of the recipient blood vessel or other anatomic conduit.

Figure 6B:
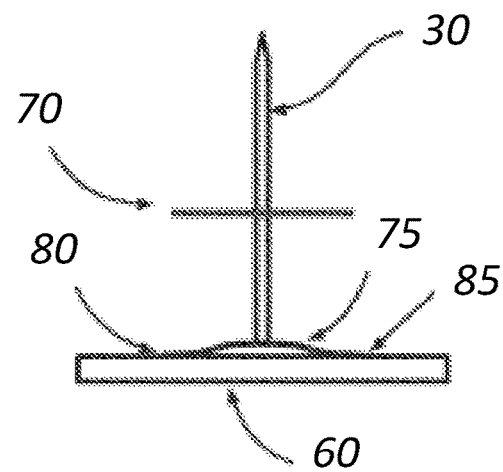

In FIGS. 6A and 6B, said retention tine 30 may be welded or otherwise affixed to a pre-tensioned tine mounting element 75 that serves to exert an outward radial force on its related retention tine 30 upon deployment. As shown in FIGS. 6A and 6B, the pre-tensioned tine mounting element 75 has two ends 80 and 85. In the embodiment of the present disclosure as shown in FIGS. 6A and 6B, end 80 is welded or permanently affixed to the surface of the sealer band 60 (also called sealer belt 60) and end 85 is free to slide across the surface of the sealer band 60 when longitudinal force is applied to the associated retention tine 30.

Figure 6C:
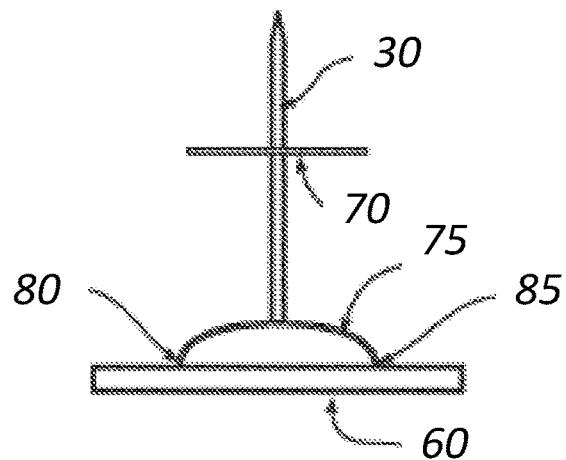
Figure 6D:
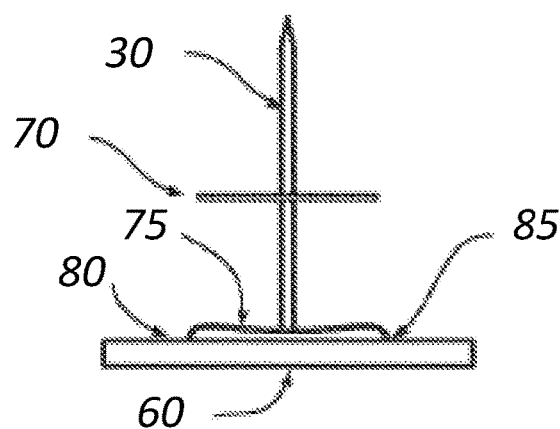

In FIGS. 6C and 6D, said retention tine 30 may be welded or otherwise affixed to a pre-tensioned tine mounting element 75 that serves to exert an outward radial force on its related retention tine 30 upon deployment. As shown in FIGS. 6C and 6D, the pre-tensioned tine mounting element 75 has two ends 80 and 85. In the embodiment of the present disclosure as shown in FIGS. 6C and 6D, both ends 80 and 85 are welded or permanently affixed to the surface of the sealer band 60.

The pre-tensioned tine mounting elements 75 as shown in FIGS. 6A-6D maintain radial tension that allows such an embodiment of the present disclosure to automatically provide a fixed amount of adjustment in the event of post-implantation remodeling and dilation of the aorta or recipient blood vessel or anatomic conduit.

Figure 7C:
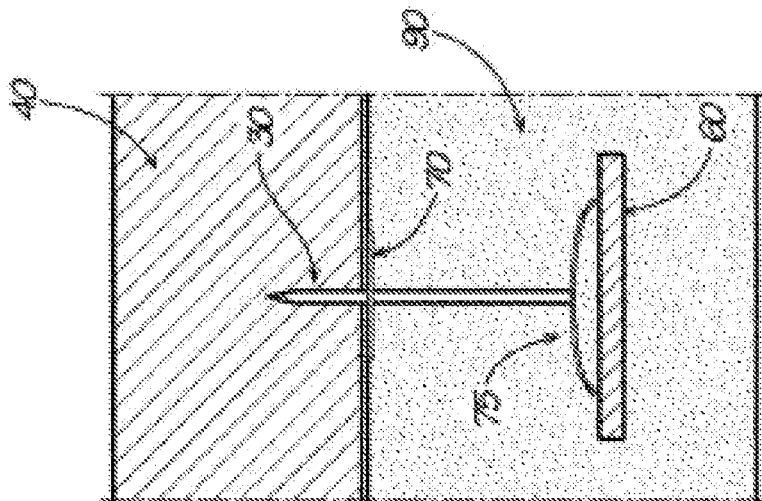
FIG. 7C is a detailed cross sectional view of an exemplary embodiment of spring-loaded remodeling attachment member deployed into an aortic wall through a compressed foam gasket with a spring-loaded remodeling attachment at full extension to accommodate aortic remodeling according to the present disclosure.
Figure 7B:
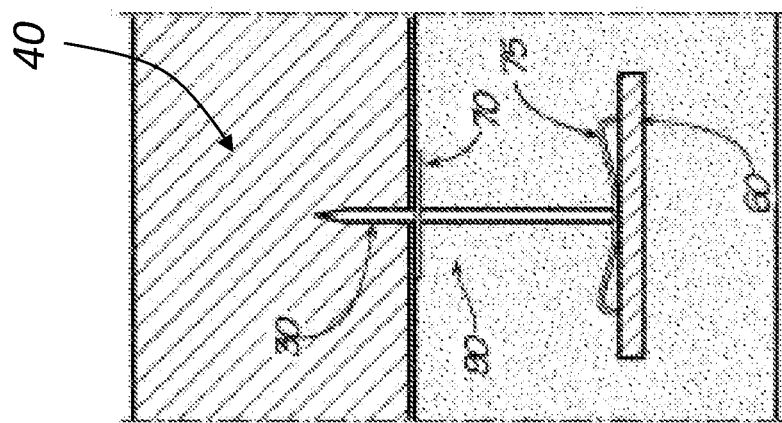
FIG. 7B is a detailed cross sectional view of an exemplary embodiment of spring-loaded remodeling attachment member deployed into an aortic wall through a compressed foam gasket with a spring-loaded remodeling attachment at full tension according to the present disclosure.
Figure 7A:
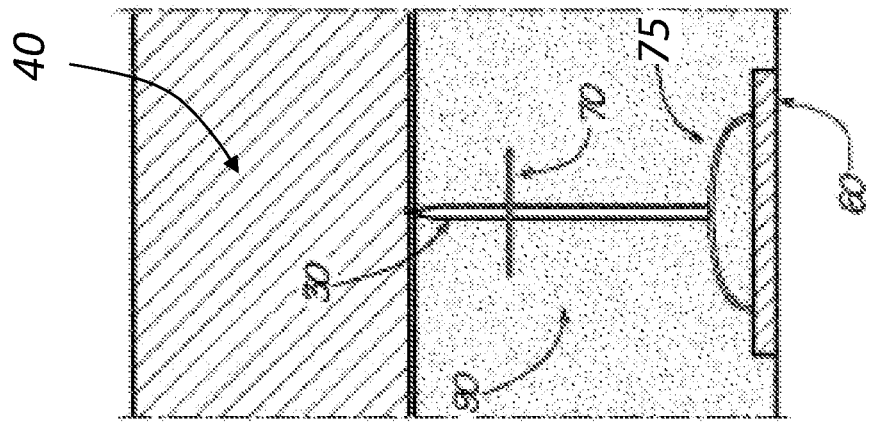
FIG. 7A is a detailed cross sectional view of an exemplary embodiment of spring-loaded remodeling attachment member contained within an uncompressed foam gasket according to the present disclosure.

FIGS. 7A-7C show the relationship among the retention tines 30, pre-tensioned spring elements 75, compressible foam gasket 90, and aortic wall 40 in an exemplary embodiment according to the present disclosure.

FIG. 7A is a detailed cross sectional view of an exemplary embodiment of spring-loaded remodeling attachment member contained within an uncompressed foam gasket according to the present disclosure. In FIG. 7A, a retention tine 30 with a tine limiter element 70 is shown attached to a sealer band 60 by a pre-tensioned spring element 75. As shown in FIG. 7A, the retention tine is completely covered by the foam gasket 90 in an uncompressed or pre-deployment condition.

Upon deployment, as shown in FIG. 7B, the foam gasket 90 is compressed between the sealer band 60 and the aortic wall 40, with penetration of the retention tine 30 into the aortic wall 40. The extent of penetration of the retention tine 30 into the aortic wall 40 is limited by a tine limiter element 70 as shown In FIGS. 7B and 7C. FIG. 7B shows the pre-tensioned spring element 75 at maximal tension.

FIG. 7C is a detailed cross sectional view of the same exemplary embodiment as shown in FIG. 7B, with deployment of retention tines 30 into an aortic wall 40 through a compressed foam gasket 90 with full extension of the pre-tensioned spring element 75 to accommodate aortic remodeling according to the present disclosure.

The embodiments of the retention tines as shown in the present drawings show the retention tines to be substantially straight, and at about ninety degree angles relative to the sealer band 60. However, other embodiments on the present disclosure may comprise curved or otherwise angled retention tines, or retention tines that may be constructed of Nitinol or other shape/memory materials so that such retention tines become angled or curved upon deployment to further strengthen the attachment of said retention tines to the aortic walls or other recipient anatomic tissues. The retention tines in various embodiments of endografts of the present disclosure may be of any cross-sectional shape, and may further be terminally rounded, sharpened, tapered, or hooked, In still further embodiments of the retention tines in endografts of the present disclosure, the retention tines may be barbed or non-barbed. Furthermore, the number of retention tines associated with a sealer band in various embodiments of the present disclosure may vary. Preferred embodiments of sealer bands or sealable circumferential collars of this disclosure comprise at least two retention tines. Moreover, the retention tines in endografts of the present disclosure may be provided as separate components that are affixed to the sealer bands or sealable circumferential collars, or they may be fabricated as integral components thereof.

FIGS. 8A-8D provide detailed views of several alternate exemplary embodiments of spring-loaded remodeling attachment members according to this disclosure.

Figure 8A:
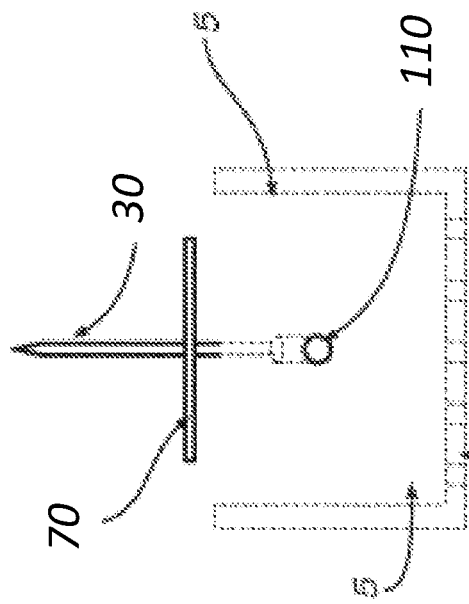
FIGS. 8A-8D are detailed views of several alternate exemplary embodiments of spring-loaded remodeling attachment members according to the present disclosure.

FIG. 8A shows a cross section of an embodiment of a sealer belt with attached retention tines according to the present disclosure. In FIG. 8A, a retention tine 30 with a tine limiter element 70 is affixed to a support element 105 which in turn is affixed to sealer belt channel side walls 5 which are connected to a sealer belt 60. Elements may be affixed in this and other embodiments of the present disclosure by any means, including but not limited to welding, cementing, or mechanical fixation. A support element 105 in various embodiments of the present disclosure may further be inserted into and retained in bores or detents in the sealer belt channel side walls 5 (not shown in FIG. 8A). Alternately still, in some embodiments of the present disclosure, a retention tine 30 may be cast or otherwise fabricated as a single unit with a support element 105.

In various embodiments of the present disclosure, a sealer belt 60 and sealer belt channel side walls 5 may form a channel of angles ranging from about 10.degree. to about 170.degree.; more preferably from about 40.degree. to about 140.degree.; and most preferably about 90.degree. In other embodiments of the present disclosure, a sealer belt 60 and sealer belt channel side walls 5 may form a continuous structure which may be circular, ovoid, semi-circular, or semi-ovoid on cross section.

Also, in various embodiments of this disclosure, the support element 105 may be a rigid structure or it may be a pre-tensioned spring. Similarly, in various embodiments of the present disclosure, the retention tine 30 may be straight (as shown in FIG. 8A) or it may be curved or helical in some or all its length. A retention tine 30 of the present disclosure may be fabricated from a shape memory material such as Nitinol or other metals, metal alloys, ceramics, plastics, or combinations thereof with shape memory characteristics to allow such a retention tine 30 to restore and maintain a desired shape upon its deployment.

Figure 8B:
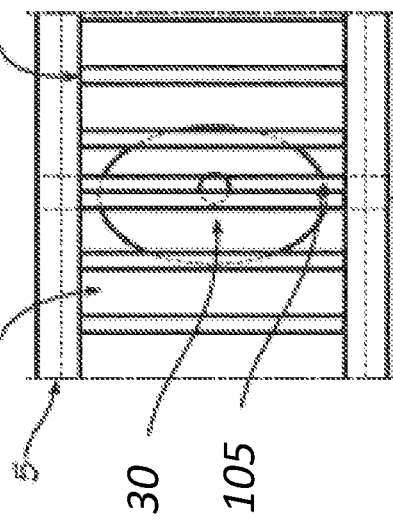

FIG. 8B shows a side view of the sealer belt with attached retention tines of FIG. 8A. In FIG. 8B, a retention bore 110 is shown in a sealer belt channel side wall 5 where it receives and retains the support element 105 and supports the retention tine 30 with a tine limiter element 70. Also in FIG. 8B, the sealer belt 60 is shown to comprise a plurality of uniformly distributed sealer gear retainment slots 62 therewithin configured to receive the teeth of a sealer gear [not shown in FIG. 8B].

Figure 8C:
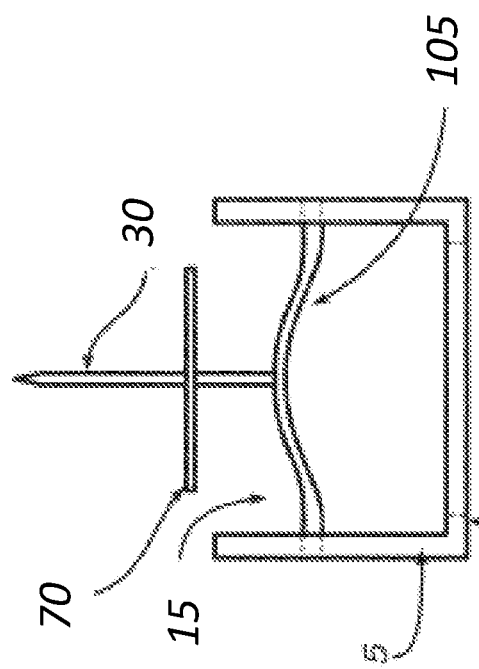

FIG. 8C shows a top view of FIG. 8A, with a retention tine 30 with a tine limiter element 70 affixed to a support element 105 which in turn is affixed to sealer belt channel side walls 5 which are connected to a sealer belt 60 with a plurality of uniformly distributed sealer gear retainment slots 62.

Figure 8D:
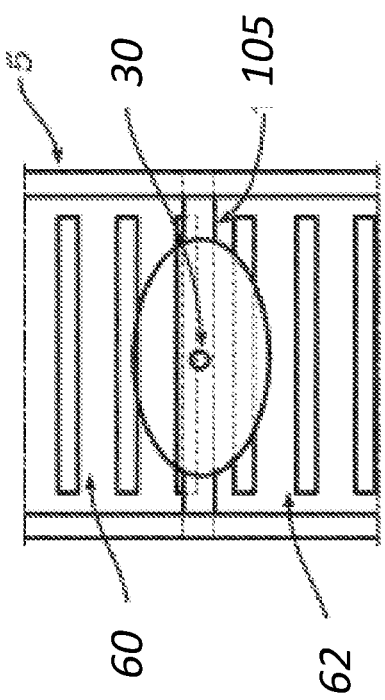

FIG. 8D similarly shows a top view of the sealer belt with attached retention tines of FIG. 8B, with a retention bore 110 shown in a sealer belt channel side wall 5 where it receives and retains the support element 105 and supports the retention tine 30 with a tine limiter element 70. Also in FIG. 8D, the sealer belt 60 is shown to comprise a plurality of uniformly distributed sealer gear retainment slots 62 therewithin configured to receive the teeth of a sealer gear [not shown in FIG. 8D].

Figure 9A:
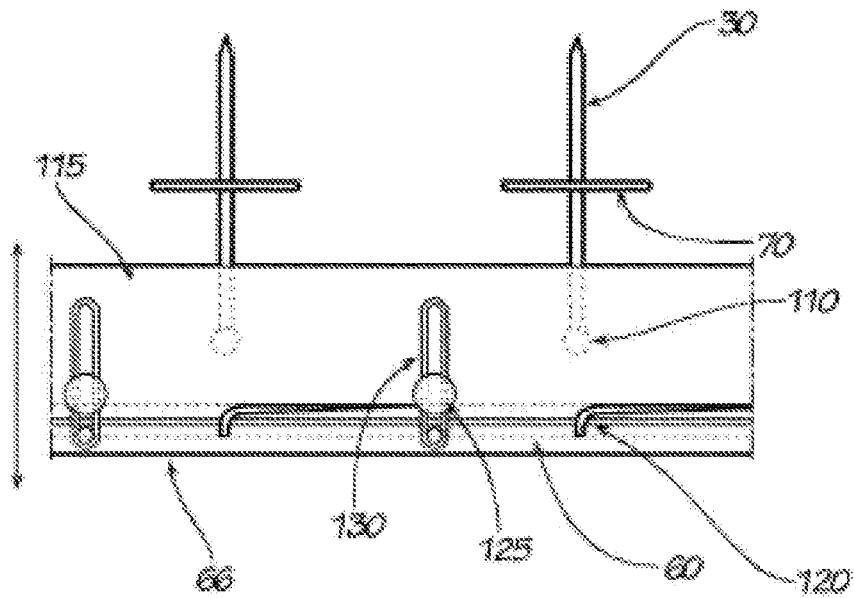
FIGS. 9A and 9B are detailed views of another exemplary embodiment of spring-loaded remodeling attachment members according to the present disclosure, in which the band containing attachment members is mounted to a fully compressed spring-tensioned suspension.
Figure 9B:
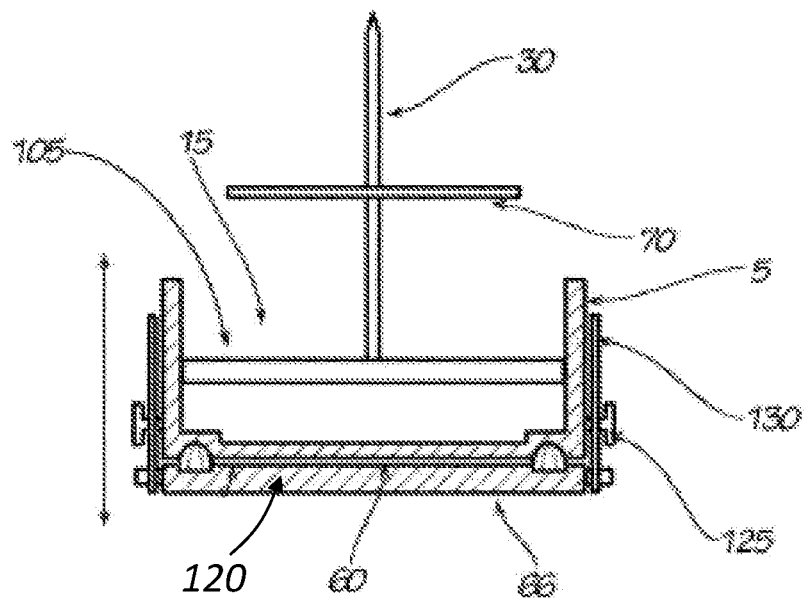

FIGS. 9A and 9B are detailed views of another exemplary embodiment of spring-loaded remodeling attachment members according to the present disclosure, in which the band containing attachment members is mounted to a spring-tensioned suspension. FIG. 9A is a lateral view of the same exemplary embodiment of spring-loaded remodeling attachment shown in cross section in FIG. 9B.

In FIGS. 9A and 9B, one or more retention tines 30 with tine limiter elements 70 are affixed to support elements 105 which in turn are affixed to sealer belt channel side walls 5 which are connected to a sealer belt 60. A retention bore 110 shown in a sealer belt channel side wall 5 where it receives and retains the support element 105 and supports the retention tine 30 with a tine limiter element 70.

In the exemplary embodiment shown in FIGS. 9A and 9B, Retention fasteners 125 affixed to the sealer belt channel side walls 5 are received and retained in slots in channel expansion elements 130. The channel expansion elements 130 are permanently affixed to a sealer belt expansion base 66, which may further be provided with a plurality of uniformly distributed sealer gear retainment slots 62 therewithin configured to receive the teeth of a sealer gear [not shown in FIG. 9A or B]. Separating the sealer belt 60 and sealer belt expansion base 66 are one or more expansion spring elements 120 which exert a spring-loaded tension between the sealer belt 60 and sealer belt expansion base 66. In FIGS. 9A and 9B, the one or more expansion spring elements 120 are shown in a compressed or non extended state, with close approximation between the sealer belt 60 and sealer belt expansion base 66.

Retention fasteners 125 as used in the present disclosure may be screws, rivets, pins, or other fasteners, and may be affixed to the sealer belt channel side walls 5 by welding, adhesives, screw threads rivets, or other known means of attaching.

Figure 10A:
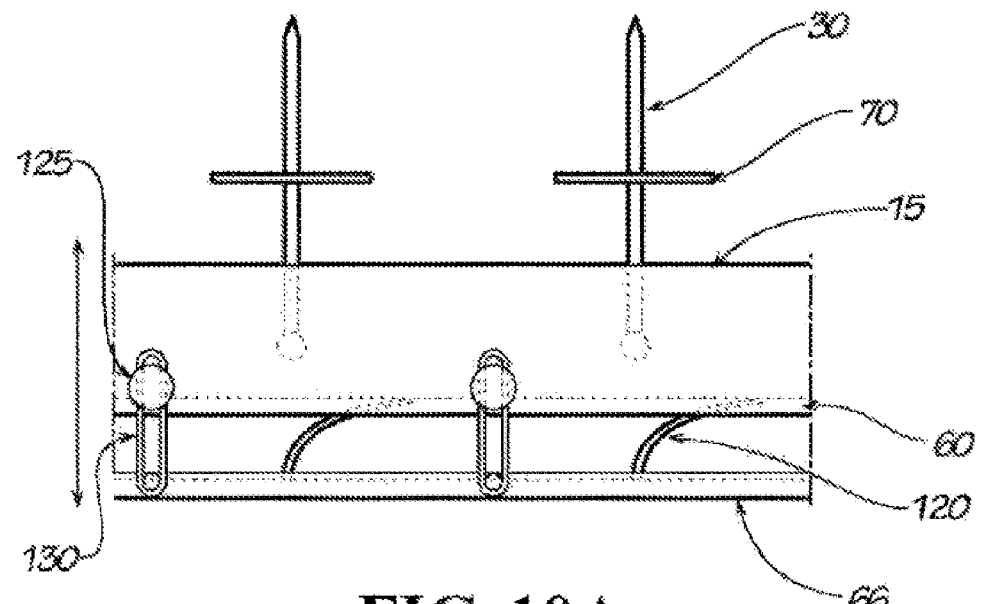
FIGS. 10A and 10B are detailed views of the exemplary embodiment of spring-loaded remodeling attachment members illustrated in FIGS. 9A and 9B according to the present disclosure, in which the band containing attachment members is mounted to a nearly fully extended spring-tensioned suspension.
Figure 10B:
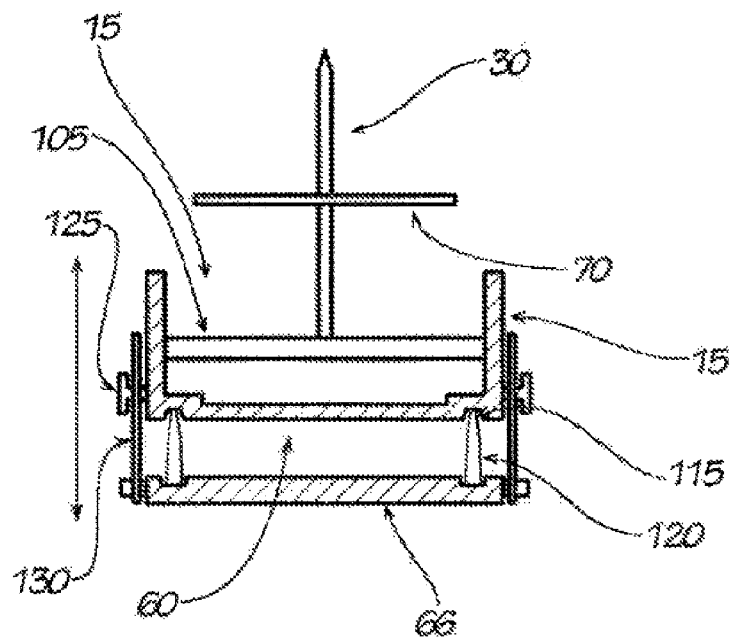

FIGS. 10A and 10B are detailed views of the same exemplary embodiment of spring-loaded remodeling attachment members according to the present disclosure as shown in FIGS. 9A and 9B, but showing the one or more expansion spring elements 120 in a decompressed or fully extended state, with near maximum separation between the sealer belt 60 and sealer belt expansion base 66. Separation between the sealer belt 60 and sealer belt expansion base 66 is limited by the amount of distance allowed by the sliding action of the retention fasteners 125 within the slots of the channel expansion elements 130.

In the exemplary embodiment of spring-loaded remodeling attachment members according to the present disclosure as shown in FIGS. 9A, 9B, 10A, and 10B, any enlargement in the diameter of the recipient anatomic conduit or blood vessel such as post-implantation aortic remodeling would allow the embodiment as shown to automatically accommodate the enlargement and maintain a leak proof seal using the spring tensioned suspension to the limit of the expansion capacity of that suspension.

Figure 11:
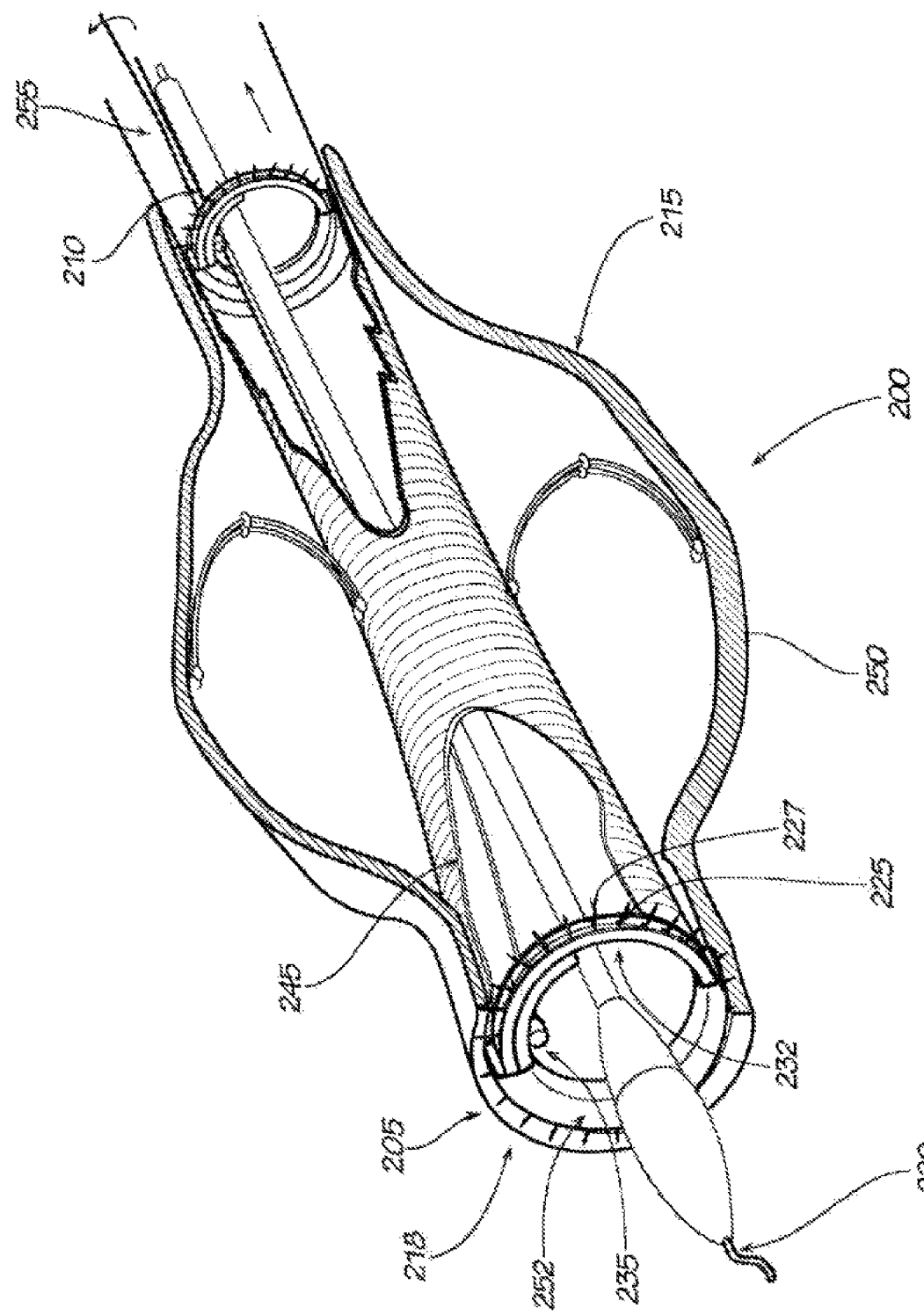
FIG. 11 is a perspective view of an embodiment of an implant interface with circumferential sealable collars and a variable sealing device with a re-docking mechanism according to the present disclosure, with the re-docking mechanism not connected to a removable re-docking control lead.

FIG. 11 is a perspective view of an embodiment of an implant interface with a circumferential sealable collars and a variable sealing device with a re-docking mechanism according to the present disclosure, with the re-docking mechanism not connected to a removable re-docking control lead.

A re-docking mechanism is desirable, should post-implantation changes in the position or size of the implant be desired to either prevent leakages or provide a more advantageous anatomic position.

In FIG. 11, an exemplary endovascular implant graft 200 of this disclosure is shown in an anatomic position within aortic walls 218 and traversing an aneurysm sac 215, said graft comprising a proximal end 205 and a distal end 210. An injection catheter 220 is shown extending through the proximal end 205 of the exemplary endovascular implant graft 200. A tubular corrugated fabric graft 250 is joined proximally by a proximal elastic sealable collar 252. Within the proximal elastic sealable collar 252 are contained a sealer belt 230 provided in an overlapping loop and with a sealer belt channel 225 therewithin, a plurality of retention tines 227 and a compressive foam gasket 240 within the sealer belt channel 225, and a sealing device housing 235. Extending distally within the lumen of the tubular corrugated fabric graft 250 is a re-dockable implant control lead 245.

Figure 12:
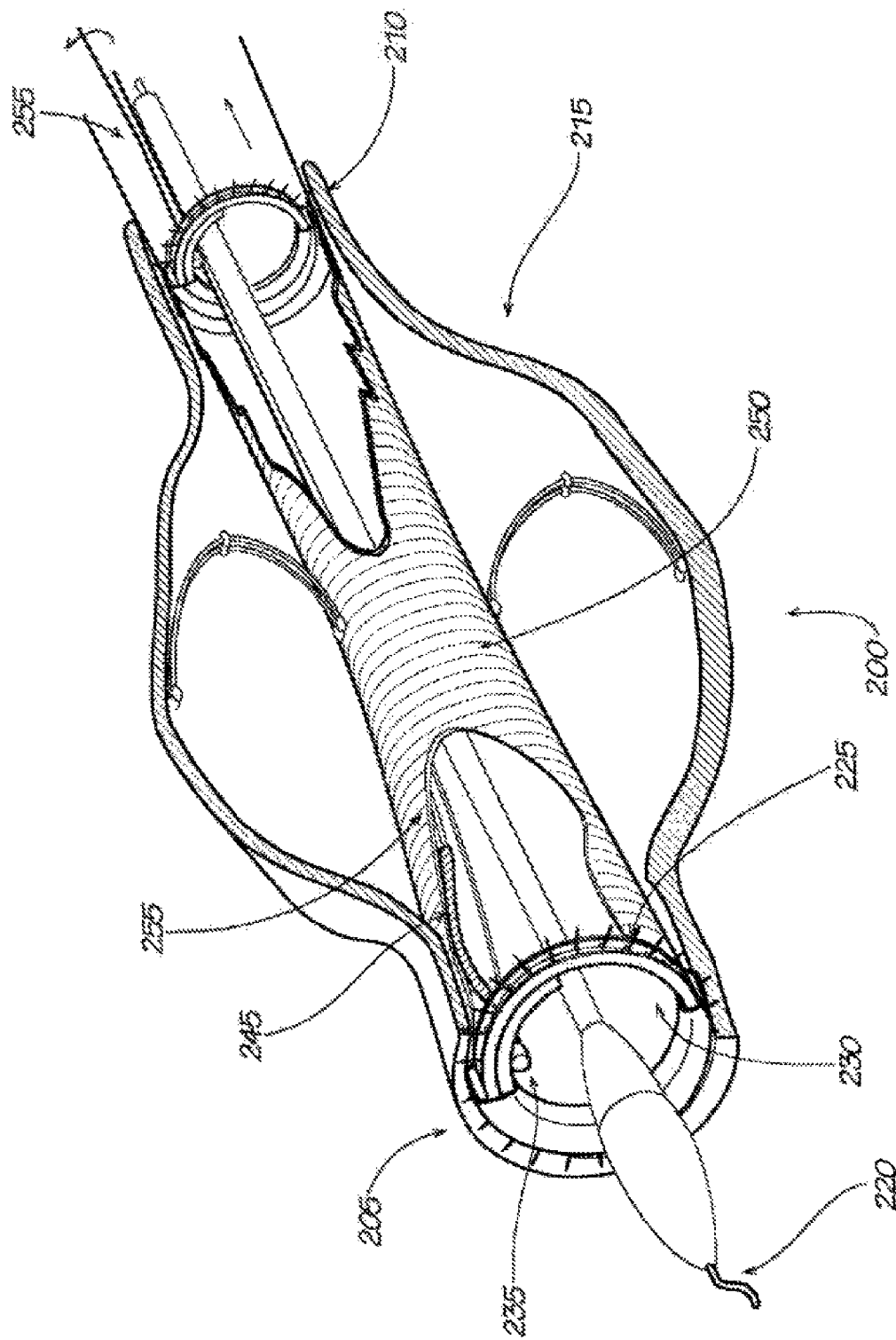
FIG. 12 is a perspective view of an embodiment of an implant interface with a circumferential sealable collars and a variable sealing device with a re-docking mechanism according to the present disclosure, with the re-docking mechanism engaged by a removable re-docking control lead.

FIG. 12 is a perspective view of an embodiment of the same exemplary endovascular implant graft 200 of the present disclosure as shown in FIG. 11, but with a removable re-docking control lead 255 engaged with the re-dockable implant control lead 245. The re-docking control lead 255 as shown in FIG. 12 has been placed into the blood vessel through a distal arteriotomy site (not shown in FIG. 12) by an operator who retains external operative control to allow re-docking and the desired alteration in the configuration and deployment of the endovascular implant graft 200.

Re-docking of the re-dockable implant control lead 245 with a removable re-docking control lead 255 may be achieved by one of several mechanisms according to the present disclosure. The re-dockable implant control lead 245 may be provided with a helix, loop, or distal hook [not shown in the figures herein] that may be snared or otherwise engaged by a guide wire or by the removable re-docking control lead 255. Alternately, magnetic and/or electromagnetic attraction may be employed between the re-dockable implant control lead 245 and the removable re-docking control lead 255 to allow their engagement in a high flow vascular environment. Alternately still, imaging technologies such as intravascular ultrasound and/or optical coherence tomography may be employed to allow an operator using basic endovascular invasive techniques to re-dock and interface with the re-dockable implant control lead 245 post-implantation.

Figure 14:
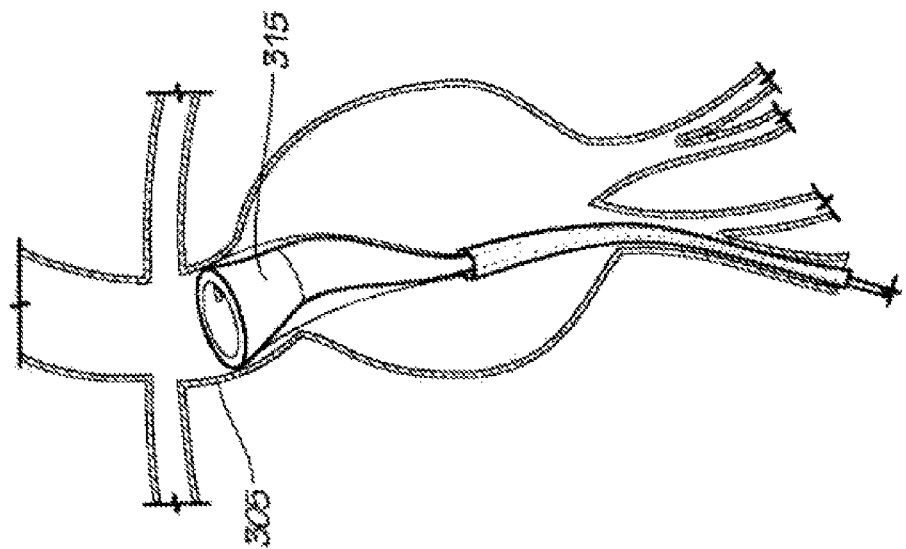
FIG. 14 is a perspective anatomic view of the embodiment of an endograft implant shown in FIG. 13 in which the implant delivery mechanism has been steered to an angular plane of delivery.
Figure 13:
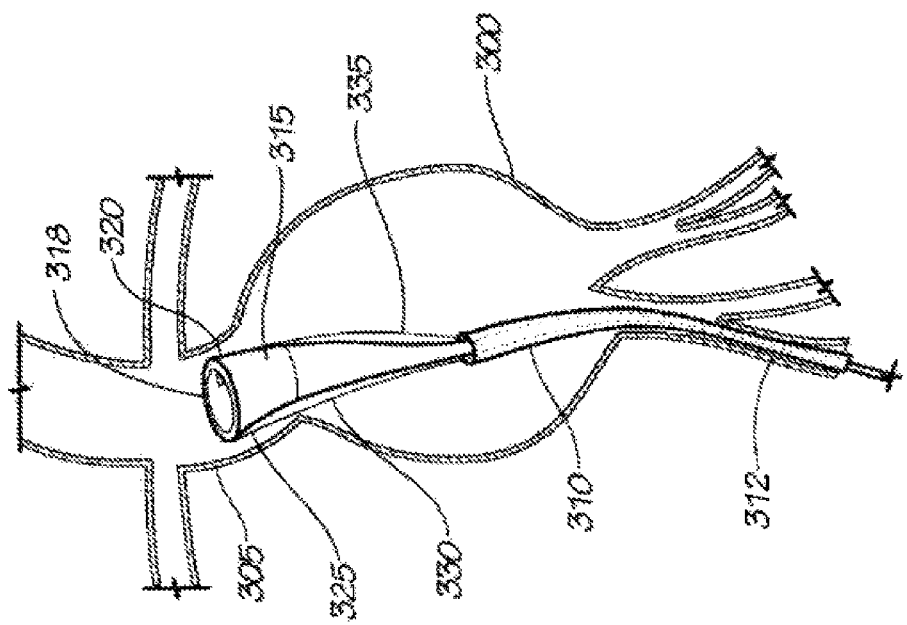
FIG. 13 is a perspective anatomic view of an embodiment of an endograft implant according to the present disclosure in which the implant delivery mechanism is remotely steerable to allow a variable plane of delivery for implantation.
Figure 15:
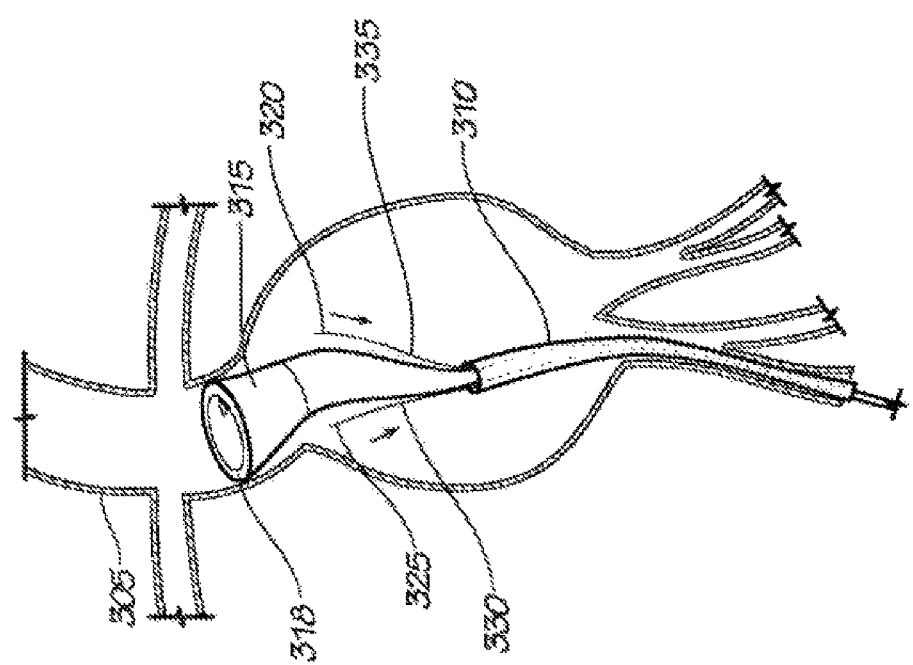
FIG. 15 is a perspective anatomic view of the embodiment of an endograft implant shown in FIG. 14 in which the implant has been sealed and delivered in a desired angular site and the steering mechanism has been disengaged from the implant and is being removed through the delivery catheter.

FIGS. 13-15 show perspective anatomic views of an embodiment of an endograft implant according to the present disclosure in which the implant delivery mechanism is remotely steerable to allow a variable plane of delivery for implantation. The anatomic conditions in the aorta proximal to the desired recipient site for endograft implantation may be irregular or tortuous, ideally requiring an angled deployment of an endograft's proximal interface. Conventional endograft devices do not permit such angled deliveries.

In FIG. 13, an exemplary abdominal aortic aneurysm 300 is shown with a narrow and angled proximal aortic neck 305. A delivery catheter 310 is shown arising from the right iliac artery 312. Extending partially from the delivery catheter 310 is the proximal portion of an exemplary endograft 315 of the present disclosure. As shown in FIG. 13, the endograft 315 comprises a proximal sealable circumferential collar 318 which is connected to a first control wire lead 330 with a removable first control attachment 325 and a second control wire lead 335 with a removable second control attachment 320. Multiple types of attachments are used in various embodiments of the present disclosure to attach the first control wire leads 330 and second control wire leads 335 to the endograft 315. In a preferred embodiment, a removable first control attachment 325 and a removable second control attachment 320 are provided with a coiled tip that may be attached by screw action into the proximal sealable circumferential collar 318. In one aspect and as illustrated in FIGS. 13 and 14, the first control wire lead 330 and the second control wire lead 335 can be of such strength that one control wire lead can be pulled by the operator and the other control wire lead can be pushed by the operator, to achieve the desired angle to accommodate a proper seal.

FIG. 14 shows the endograft implant of FIG. 13 in which the endograft 315 has been steered to a desired angular plane of delivery. Thus, the control wire leads have been used to achieve and maintain a proper proximal seal angle, which is maintained while the gasket is enlarged and the seal is achieved by deploying the times.

FIG. 15 shows the endograft implant of FIG. 14 in which the proximal sealable circumferential collar 318 has been delivered to the desired angular site in the proximal aorta 305 and a seal has been accomplished according to the present disclosure by mechanical alteration of the proximal sealable circumferential collar 318 to seal against and then attach to the aortic wall 305. In FIG. 15, the tines have been deployed, and the removable first control attachment 325 and the removable second control attachment 320 are shown disengaged from the proximal sealable circumferential collar 318. Also in FIG. 15, the first control wire lead 330, the removable first control attachment 325, the second control wire lead 335, and the removable second control attachment 320 are shown being removed through the delivery catheter 310.

Figure 16:
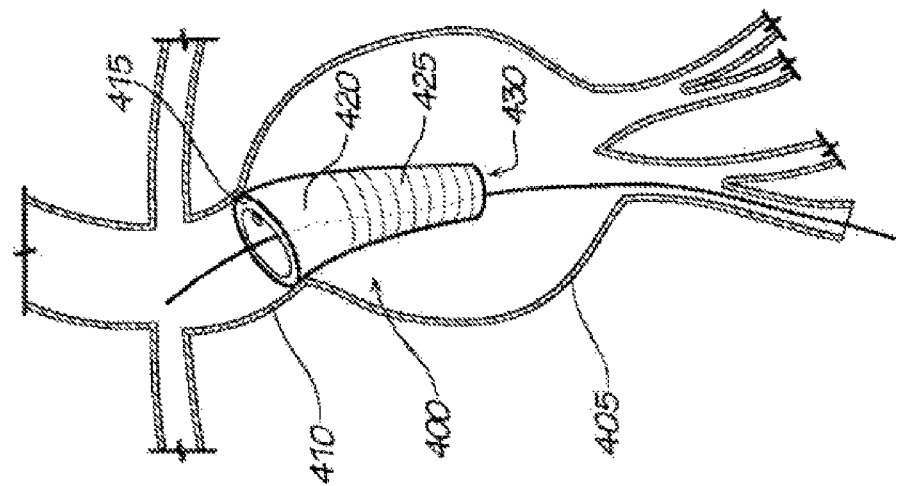
FIG. 16 shows a perspective anatomic view of an exemplary embodiment of an endograft implant according to the present disclosure in which the implant is a universal proximal cuff implant for treatment of an abdominal aortic aneurysm.

FIG. 16 shows a perspective anatomic view of an exemplary embodiment of an endograft implant according to this disclosure in which the implant is a universal proximal cuff endovascular implant for treatment of an abdominal aortic aneurysm. Endografts with the features shown in the various embodiments of the present disclosure have unique abilities to accommodate to anatomic variations that would preclude or compromise use of conventional endograft systems. For example, non-conducive anatomy can arise by virtue of angulation, calcific disease, thrombus, or a short neck. The universal proximal cuff implants of the present disclosure allow an operator to make use of their ability to securely seal and attach in anatomic sites where conventional endografts cannot be securely placed, and then allow a conventional endograft to securely dock with the universal proximal cuff endovascular implants distally.

In FIG. 16, a universal proximal cuff endovascular implant 400 has been placed in a narrow and angulated proximal aortic neck 410 and extends into an abdominal aortic aneurysm 405. The universal proximal cuff endovascular implant 400 comprises a proximal sealable circumferential collar 415 of the present disclosure, which is connected to an elastic proximal end 420 of a non-elastic tubular implant body 425 with a distal docking opening 430. The device of FIG. 16 has been delivered and implanted with the techniques of this disclosure, and contains a variable sealing device and attachment retention tines of this disclosure (not shown in FIG. 16). Once the device of FIG. 16 has been implanted as shown, an operator may engage and deliver any endograft including conventional endografts to the distal docking opening 430. Thus, the universal proximal cuff endovascular implant 400 provides a conduit that is suspended into, or extends into, the into an abdominal aortic aneurysm 405, that can serve as a neck conducive for docking any known endograft.

Figure 17:
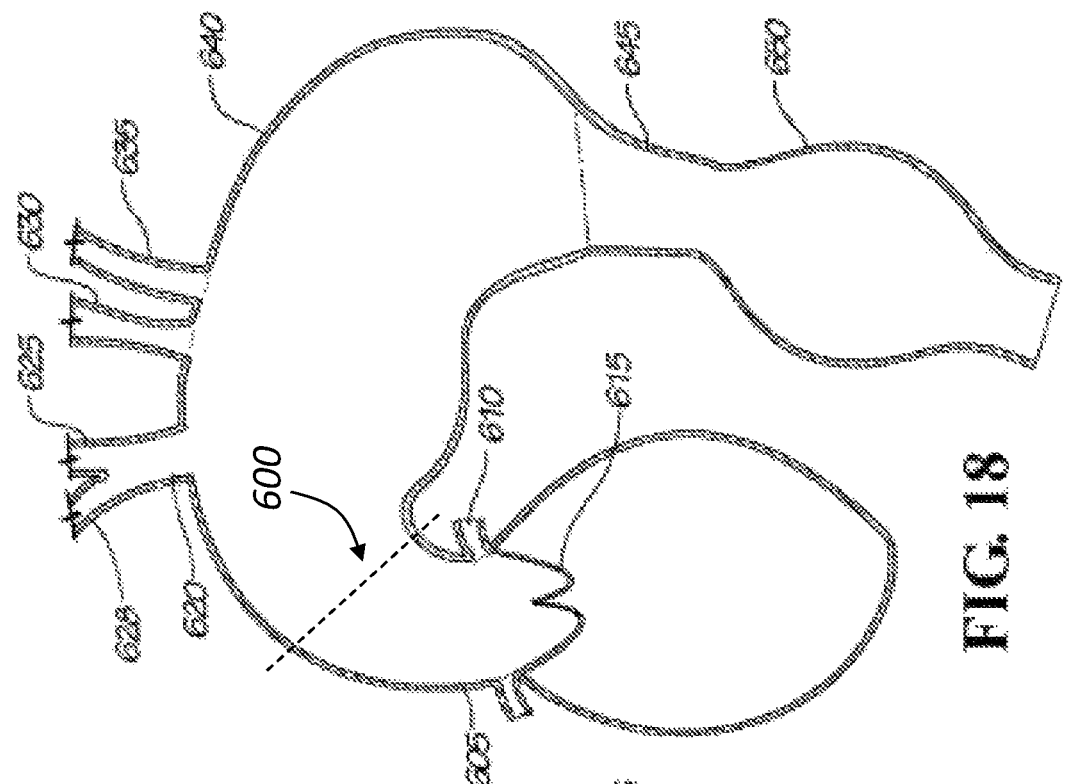
FIG. 17 shows a perspective anatomic view of an exemplary embodiment of an endograft implant according to the present disclosure in which the implant is a universal proximal cuff implant for treatment of a thoracic aortic aneurysm.

FIG. 17 shows a perspective anatomic view of an exemplary embodiment of an endograft implant according to the present disclosure in which the implant is a universal proximal cuff endovascular implant for treatment of a thoracic aortic aneurysm.

In FIG. 17, a universal proximal cuff endovascular implant 500 has been placed in a narrow and angulated proximal aortic neck 510 and extends into a descending thoracic aortic aneurysm 505. The universal proximal cuff endovascular implant 500 comprises a proximal sealable circumferential collar 515 of the present disclosure, which is connected to an elastic proximal end 520 of a non-elastic tubular implant body 525 with a distal docking opening 530. The device of FIG. 17 has been delivered and implanted with the techniques of the present disclosure, and contains a variable sealing device and attachment retention tines of the present disclosure (not shown in FIG. 16). Once the device of FIG. 17 has been implanted as shown, an operator may engage and deliver any endograft including conventional endografts to the distal docking opening 530. FIG. 17 shows such a delivery in progress, with a guide wire 535 in place, and a delivery catheter 540 containing an endograft being introduced for delivery into the distal docking opening 530.

Figure 18:
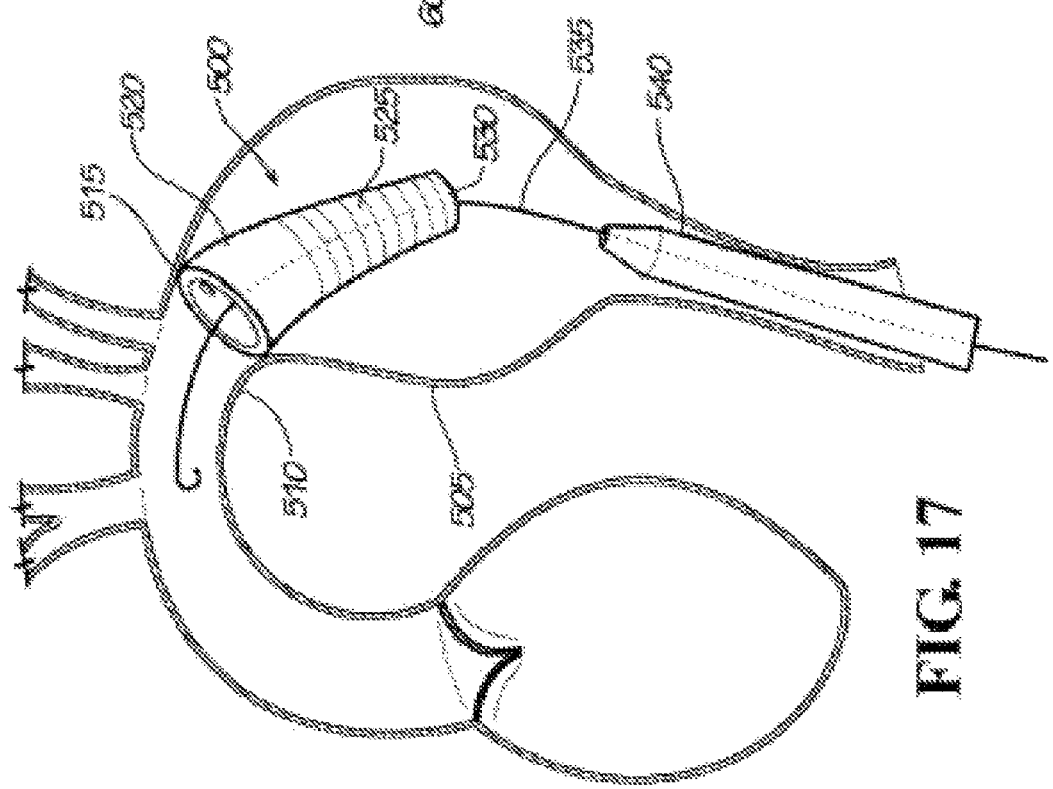
FIG. 18 is an anatomic drawing which shows a complex aortic arch with a first aneurysm involving the aortic arch and a second aneurysm involving the descending aorta.
Figure 20:
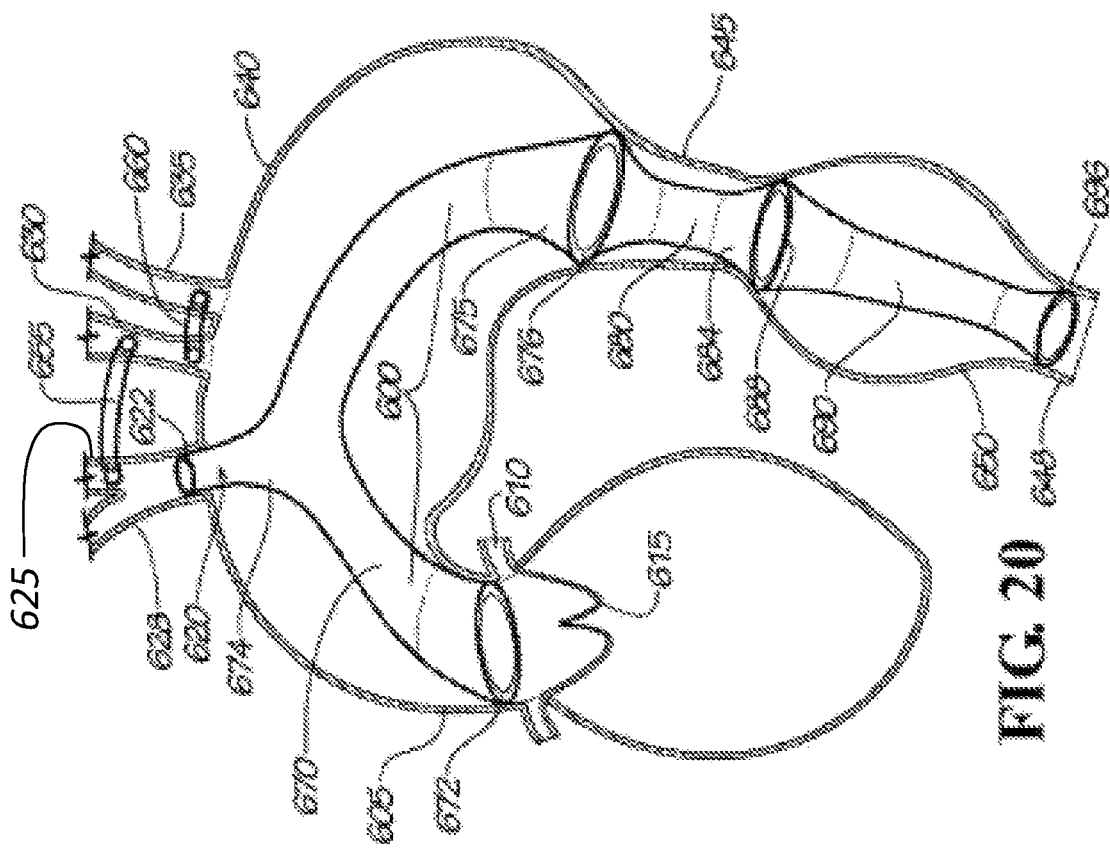
FIG. 20 shows the same view as FIG. 19, with exemplary endovascular placement of three embodiments of endografts of the present disclosure to traverse the pathology and maintain vital circulation.
Figure 19:
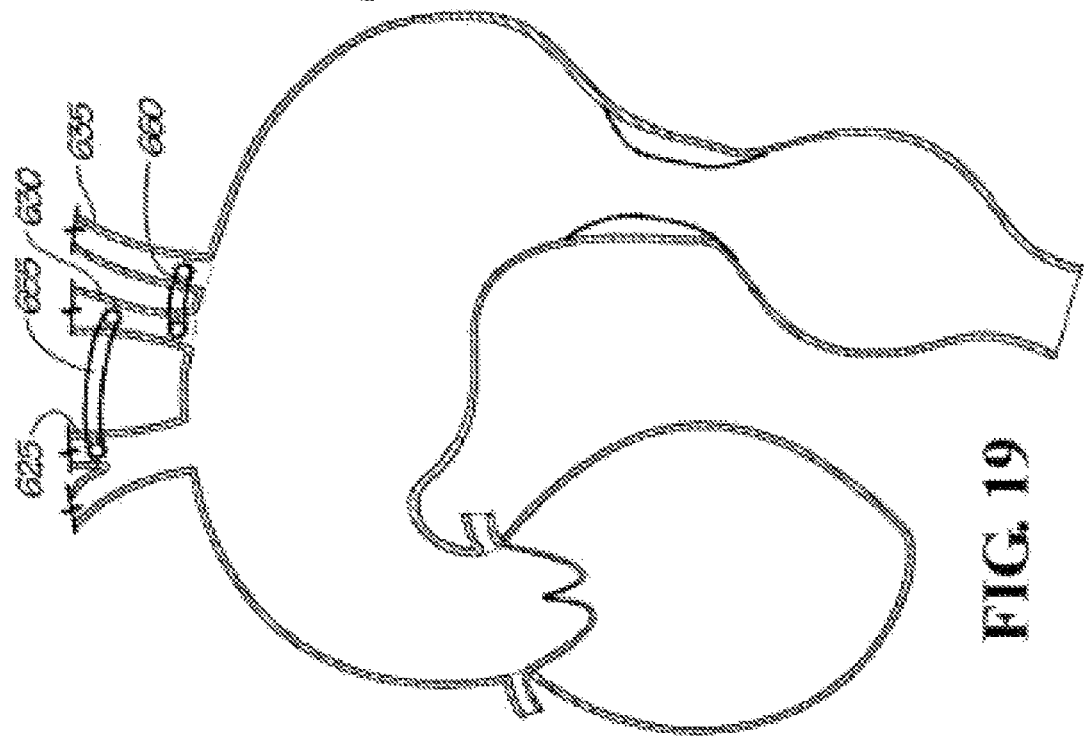
FIG. 19 shows the anatomic situation of FIG. 18, in which extra-anatomic surgical bypass has been performed with bypasses between the right and left carotid and between the left carotid and left subclavian arteries.

FIGS. 18-20 show an exemplary pathologic condition with a complex aortic arch with a first aneurysm involving the aortic arch and a second aneurysm involving the descending aorta. Such a condition would not be treatable with conventional endografts. In FIG. 18, the ascending aorta 605 arises above the aortic valve 615 and gives off the coronary arteries 610. The area between the ascending aorta 605 and the descending thoracic aorta 645 is the aortic arch 600. The aortic arch 600 gives rise to the innominate artery 620 which divides into the right subclavian artery 628 and right common carotid artery 625, The aortic arch 600 further gives rise to the left common carotid artery 630 and the left subclavian artery 635. The right subclavian artery 628, right common carotid artery 625, left common carotid artery 630 and the left subclavian artery 635 are critical blood vessels to supply arterial blood to the arms, head, neck, and brain. FIG. 18 further shows a large first aneurysm 640 involving the aortic arch 600 and a second aneurysm 650 involving the descending thoracic aorta 645.

FIG. 19 shows the anatomic situation of FIG. 18, in which extra-anatomic surgical bypass has been performed with a first bypass 655 between the right common carotid artery 625 and left common carotid artery 630 and a second bypass 660 between the left common carotid artery 630 and the left subclavian artery 635.

FIG. 20 shows the same view as FIG. 19, with exemplary endovascular placement of three embodiments of endografts of the present disclosure to traverse the pathology and maintain vital circulation.

In FIG. 20, a first endograft 670 of the present disclosure has been placed through the aortic arch 600 with an attachment in the ascending aorta just distal to the coronary arteries using a first proximal sealable circumferential collar 672 of the present disclosure. The first endograft 670 as shown has an innominate branch 620 with an innominate sealable circumferential collar 622. The first endograft 670 traverses and excludes the first aneurysm 640 and terminates in a distal cuff 675 at the distal end of the aortic arch 600. A second endograft 680 connects to the distal cuff 675 of the first endograft 670 using a second proximal sealable circumferential collar 676 of the present disclosure's design.

As shown in FIG. 20, the second endograft 680 traverses a segment of the descending aorta 645. The second endograft 680 may be fenestrated [not shown in FIG. 20] either in manufacture or surgically to allow collateral circulation to be maintained to the spinal and other vessels arising from that segment of the descending aorta 645.

FIG. 20 further shows a second aneurysm 650 in the descending aorta 645. In FIG. 20, this is traversed and excluded by a third endograft 690 of the present disclosure, which is shown sealably attaching to the second endograft distal cuff 684 with a third proximal sealable circumferential collar 688 of the present disclosure's design. The third endograft 690 is shown attaching distally with a distal sealable circumferential collar 696 of the present disclosure's design.

Thus, in FIG. 20, circulation is maintained to the arms, head, brain, and spine, while excluding two difficult thoracic aneurysms. This exemplary combination of endografts of the present disclosure and a relatively minor vascular procedure allows complete treatment of very difficult anatomic pathology that would be beyond the reach of conventional endovascular techniques and devices. This makes a variety of aortic arch pathologies within the scope of the devices and methods of this disclosure, including aortic arch aneurysms, dissecting aneurysms of the aortic arch, transposition of the great vessels, and other complex pathologies.

In addition to the making and use of endovascular implant grafts, other anatomic applications are also within the scope of the present disclosure. As an example, the mechanisms and principles disclosed herein may be applied to gastrointestinal disorders, where an intralumenal bypass may be desirable that may be placed using endoscopic techniques.

Crohn's disease (also known as regional) is a chronic, episodic, inflammatory bowel disease (IBD) and is generally classified as an autoimmune disease. Crohn's disease can affect any part of the gastrointestinal tract from mouth to anus; as a result, the symptoms of Crohn's disease vary among afflicted individuals. The disease is characterized by areas of inflammation with areas of normal lining between in a symptom known as skip lesions. The main gastrointestinal symptoms are abdominal pain, diarrhea (which may be bloody, though this may not be visible to the naked eye), constipation, vomiting, weight loss or weight gain. Crohn's disease typically involves the terminal ileum.

In an exemplary embodiment of a gastrointestinal aspect of the present disclosure, a tubular graft comprising proximal and distal sealable implant interfaces as disclosed herein is endoscopically placed and affixed proximally to and distally to a segment of intestine affected by Crohn's disease to divert the intestinal contents therethrough.

By providing an intraintestinal bypass for the conduit of intestinal contents though areas affected by Crohn's disease, local inflammatory response and sequelae in the affected areas are reduced.

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. Therefore, the description and examples presented herein should not be construed to limit the scope of the present disclosure.

Co-pending U.S. patent application Ser. No. 11/888,009, filed Jul. 31, 2007, is incorporated by reference herein in its entirety. Any other publications and patents mentioned in this disclosure are incorporated herein by reference in their entireties, for the purpose of describing and disclosing the constructs and methodologies described in those publications and patents, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that may be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

We claim:

1. An implantable vascular device, comprising:
   a tubular implant body having a sealable circumferential collar and a housing, wherein the sealable circumferential collar has a first end portion and a second end portion, and wherein the housing is coupled to the first end portion of the sealable circumferential collar;
   a variable sealing device having a rotatable member coupled to the housing of the tubular implant body and to the second end portion of the sealable circumferential collar, wherein the variable sealing device is configured such that rotating the rotatable member in a first direction relative to the housing and the second end portion of the sealable circumferential collar circumferentially expands the sealable circumferential collar and such that rotating the rotatable member in a second direction relative to the housing and the second end portion of the sealable circumferential collar circumferentially contracts the sealable circumferential collar; and
   a locking member coupled to the rotatable member of the variable sealing device, wherein the locking member is configured to move between an unlocked state and a locked state,
   wherein when the locking member is in the unlocked state, the locking member allows the rotatable member to be rotated in the first direction and the second direction relative to the housing and the second end portion of the sealable circumferential collar, and allows expansion and contraction of the sealable circumferential collar, and
   wherein when the locking member is in the locked state, the locking member prevents the rotatable member from being rotated in the first direction and the second direction relative to the housing and the second end portion of the sealable circumferential collar, and prevents expansion and contraction of the sealable circumferential collar.

2. The device of claim 1, wherein the rotatable member is a gear.

3. The device of claim 1, wherein the locking member comprises a spring interface and a central axel, the central axel being configured to be coupled to a rotatable shaft of a delivery apparatus.

4. The device of claim 3, wherein the locking member is configured such that the central axel of the locking member is spaced axially from the rotatable member of the variable sealing device when the locking member is in the locked state, and wherein the locking member is configured such that the central axel of the locking member engages the rotatable member of the variable sealing device when the locking member is in the unlocked state.

5. The device of claim 1, wherein the sealable circumferential collar comprises an expandable and contractible lattice formation.

6. The device of claim 1, wherein the sealable circumferential collar comprises an expandable and contractible mesh.

7. The device of claim 1, wherein the locking member is configured such that moving the locking member axially relative to the rotatable member moves the locking member between the locked state and the unlocked state.

8. The device of claim 1, further comprising a compressible foam gasket coupled to the sealable circumferential collar.

9. An implantable vascular device, comprising:
an expandable and compressible implant body having a first end portion and a second end portion;
a housing coupled to the first end portion of the implant body;
a rotatable member coupled to the housing and to the second end portion of the implant body such that rotating the rotatable member in a first direction relative to the housing and the implant body expands the implant body and such that rotating the rotatable member in a second direction relative to the housing and the implant body contracts the implant body; and
a locking member coupled to the rotatable member and configured to move between an unlocked state and a locked state,
wherein when the locking member is in the unlocked state, the locking member allows the rotatable member to be rotated in the first direction and the second direction relative to the housing and the implant body, and
wherein when the locking member is in the locked state, the locking member prevents the rotatable member from being rotated in the first direction and the second direction relative to the housing and the implant body.

10. The device of claim 9, wherein the implant body has a sealable circumferential collar comprising an expandable and contractible lattice formation.

11. The device of claim 9, wherein the implant body has a sealable circumferential collar comprising an expandable and contractible mesh.

12. The device of claim 9, wherein the locking member comprises a spring interface and a central axel, the central axel being configured to be coupled to a rotatable shaft of a delivery apparatus.

13. The device of claim 12, wherein the locking member is configured such that the central axel of the locking member is spaced axially from the rotatable member when the locking member is in the locked state, and wherein the locking member is configured such that the central axel of the locking member engages the rotatable member when the locking member is in the unlocked state.

14. An implantable vascular device, comprising:
an implant body having a sealable collar and a housing, wherein the sealable collar has a first end portion and a second end portion, and wherein the housing is coupled to the first end portion of the sealable collar;
a variable sealing device having a rotatable member coupled to the housing of the implant body and to the second end portion of the sealable collar, wherein the variable sealing device is configured such that rotating the rotatable member in a first direction relative to the housing and the second end portion of the sealable collar expands the sealable collar circumferentially and such that rotating the rotatable member in a second direction relative to the housing and the second end portion of the sealable collar contracts the sealable collar circumferentially; and
a locking mechanism having a spring interface and a central axel, wherein the central axel is configured to be coupled to a rotatable shaft of a delivery apparatus, and wherein the locking mechanism is configured to move between an unlocked state and a locked state, and
wherein when the locking mechanism is in the unlocked state, the locking mechanism allows the rotatable member to be rotated in the first direction and the second direction relative to the housing and the second end portion of the sealable collar, and allows expansion and contraction of the sealable collar, and
wherein when the locking mechanism is in the locked state, the locking mechanism prevents the rotatable member from being rotated in the first direction and the second direction relative to the housing and the second end portion of the sealable collar, and prevents expansion and contraction of the sealable collar.

15. The device of claim 14, wherein the rotatable member is a gear.

16. The device of claim 14, wherein the locking mechanism is configured such that the central axel of the locking mechanism is spaced axially from the rotatable member of the variable sealing device when the locking mechanism is in the locked state, and wherein the locking mechanism is configured such that the central axel of the locking mechanism engages the rotatable member of the variable sealing device when the locking mechanism is in the unlocked state.

17. The device of claim 14, wherein the sealable collar comprises an expandable and contractible lattice formation.

18. The device of claim 14, wherein the sealable collar comprises an expandable and contractible mesh.

19. The device of claim 14, wherein the locking mechanism is configured such that moving the locking mechanism axially relative to the rotatable member moves the locking mechanism between the locked state and the unlocked state.

20. The device of claim 14, further comprising a compressible foam gasket coupled to the sealable collar.

* * * * *